(12) United States Patent
Honjo et al.

(10) Patent No.: US 6,846,647 B1
(45) Date of Patent: Jan. 25, 2005

US006846647B1

(54) POLYPEPTIDES SUPPRESSING SMOOTH MUSCLE CELL PROLIFERATION, THE ENCODING CDNA, AND RELATED METHODS

(75) Inventors: Tasuku Honjo, Kyoto (JP); Kei Tashiro, Kyoto (JP); Tomoyuki Nakamura, San Diego, CA (US)

(73) Assignee: ONO Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/674,330
(22) PCT Filed: Apr. 28, 1999
(86) PCT No.: PCT/JP99/02283
§ 371 (c)(1), (2), (4) Date: Dec. 20, 2001
(87) PCT Pub. No.: WO99/55863
PCT Pub. Date: Nov. 4, 1999

(30) Foreign Application Priority Data

Apr. 28, 1998 (JP) .......................................... 10-119731

(51) Int. Cl.⁷ ................................................. C12Q 1/01
(52) U.S. Cl. ..................... 435/29; 435/69.1; 435/320.1; 435/252.3; 435/254.11; 435/419; 435/325; 536/23.5; 530/350
(58) Field of Search ................................ 530/300, 350; 536/23.5, 231, 232; 435/320.1, 252.3, 254.11, 419, 325, 69.1, 29; 514/12

(56) References Cited

U.S. PATENT DOCUMENTS 5,872,234 A * 2/1999 Bandman et al. .......... 536/23.1

FOREIGN PATENT DOCUMENTS

| WO | 97/38002 | 10/1997 | ........... C07K/21/00 |
|---|---|---|---|
| WO | 97/38012 | 10/1997 | ........... C07K/14/00 |
| WO | 98/46746 | 10/1998 | ........... C12N/15/12 |
| WO | 99/00405 | 1/1999 | ........... C07K/2/00 |
| WO | 99/00410 | 1/1999 | ........... C07K/14/00 |

OTHER PUBLICATIONS

Lee et al. EST 190962 Normalized rat spleen, Bento Soares Rattus sp. cDNA clone RSPAA89 5' end, mRNA sequence. GenBank Accession No. AA801465 created on Jul. 19, 1995.*
Marra et al. "ve31a08.r1 Ko mouse embryo 11 5dpc Mus musculus cDNA clone IMAGE:819734 5' similar to TR:G458228 G458228 Extracellular Protein Precursor. mRNA sequence." GenBank Accession No. AA37518 created on May 30, 1997.*
Bork et al. "From genome sequences to protein function." Current Opinion in Structural Biology (1994) 4:393–403.*
International Search Report.
Nakamura et al. DANCE, a novel secreted RGD protein expressed in developing, autherosclerotic, and balloon–injured arteries. *J. Bio. Chem.* 274(32):22476–22483 (Aug. 6, 1999).
Olsen, "Human EEGF Protein", Database Accession No.: AAW79739, Jan. 25, 1999.
Olsen, "Human EEGF Protein", Database Accession No.: AAV62432, Jan. 25, 1999.
Kowal, "Rattus norvegicus Embryonic Vascular EGF Repeat–containing Protein EVEC mRNA", Database Accession No.: AF137350, Apr. 14, 1999.

* cited by examiner

*Primary Examiner*—Richard Hutson
*Assistant Examiner*—Kathleen Kerr
(74) *Attorney, Agent, or Firm*—Sughrue Mion, PLLC

(57) ABSTRACT

The present invention provides a secreted protein (A55) produced by murine embryonic cardiac cells and a polynucleotide encoding the protein. The invention also provides a second secreted protein (A55b) produced by a splice variant of the gene encoding the first protein, and a polynucleotide encoding the variant. Finally, the invention also provides methods for utilizing the two proteins in the treatment and prevention of diseases, such as through the inhibition of proliferation of vascular smooth muscle cells and through the regulation of physiological activities including hematopoietic cell activity, tissue forming/repairing activity, activin/inhibin activity, chemotactic/chemokinetic activity, blood coagulating and thrombotic activity.

12 Claims, 1 Drawing Sheet

POLYPEPTIDES SUPPRESSING SMOOTH MUSCLE CELL PROLIFERATION, THE ENCODING CDNA, AND RELATED METHODS

FIELD OF THE INVENTION

The present invention provides a novel polypeptide, a cDNA encoding the polypeptide, and utilization thereof.

BACKGROUND OF THE INVENTION

In modern medical research, cardiovascular biology is a field that attracts considerable attention because cardiovascular disease is the leading cause of mortality. Cardiovascular research has revealed important facts about neointimal formation and arterial remodeling, both of which are thought to contribute to plaque formation in atherosclerosis and blood vessel narrowing. For example, there are three aspects of the cellular process in hypercholesterolaemia induced blood vessel damage in animal models that mimic human development of arteriosclerotic coronary disease. The three elements that form lesions on the artery wall are: a) proliferation of smooth muscle cells, macrophages and lymphocytes, b) formation of connective tissues (mainly elastic fiber proteins, collagen and proteoglycans made by smooth muscle cells in a process similar to scar formation), and c) the accumulation of lipid and cholesterol in the newly formed connective tissue matrices. The exact sequence of the three damaging elements are debatable, but it is clear that the abnormal de-differentiation, re-differentiation and growth of smooth muscle cells contribute structurally to vessel damage. Moreover, another significant pathological process that involves abnormal smooth muscle cell growth is restenosis after percutaneous transluminal coronary angioplasty (PTCA).

The present inventors made reasonable efforts by isolation of the molecules related to participation of smooth muscle cells in angiogenesis, for the goal of utilizing them for regulation of abnormal proliferation of smooth muscle cells such as is described above.

In order to obtain a certain polypeptide or cDNA coding for the same, there has been generally employed a method composed of detecting the sought after biological activity in a tissue or a cell culture medium, then identifying a polypeptide as substance of the activity through the isolation and purification and isolating a gene encoding the polypeptide or expression-cloning method to isolate a gene by access of the biological activity of the polypeptide encoded by it.

Because in many cases, however, physiologically active polypeptides have various biological activities, when taking the method to approaches based on a certain activity to isolate a gene, increasingly it has turned out that the gene is identical to a known gene which has another activity after spending much efforts to isolate it. And because, in many cases, biological factors are produced only in a very slight amount or only in a specific condition, it is often been difficult to isolate and purify a factor and detect its biological activity.

Recent rapid developments in techniques for constructing cDNAs and sequencing techniques have made it possible to quickly sequence a large amount of cDNAs. By utilizing these techniques, a process, which comprises constructing cDNAs at random, identifying the nucleotide sequences thereof, expressing novel polypeptides encoded by them, is now in progress. Although this process is advantageous in that a gene can be cloned and information regarding its nucleotide sequence can be obtained without any biochemical or genetic analysis, the target gene can be discovered thereby only accidentally in many cases.

SUMMARY OF THE INVENTION

The present inventors investigated to find novel factors (polypeptides) which are useful for study or for the treatment or diagnosis of diseases induced by abnormal proliferation of smooth muscle. Especially, we sought secreted proteins and membrane proteins which have signal sequences for secretion.

The present inventors have studied cloning method of genes coding for proliferation and/or differentiation factors functioning in hematopoietic systems and immune systems. Focusing their attention on the fact that most of the secretory proteins such as proliferation and/or differentiation factors (for example various cytokines) and membrane proteins such as receptors thereof (hereafter these proteins will be referred to generally as secretory proteins and the like) have sequences called signal peptides in the N-termini, the inventors conducted extensive studies on a process for efficiently and selectively cloning a gene coding for a signal peptide. Finally, we have successfully invented a screening method for cDNAs having sequence encoding signal peptides, we called the method a signal sequence trap (SST) (Japanese Patent Publication No. 6-315380).

We also developed a yeast SST method based on the same concept. By the method using yeast, genes including sequences encoding signal peptides can be identified more easily and effectively (U.S. Pat. No. 5,536,637).

By using the present method, the present inventors identified novel secreted proteins produced by mouse embryonic heart and a cDNA fragments encoding them, and by using the sequence information of the cDNA fragments they isolated each full-length cDNA from mouse embryonic heart and human kidney. And they discovered that the polypeptides had the ability to suppress smooth muscle cells.

The present cDNA sequence was named mouse A55 clone and isolated from cDNA library derived from mouse embryonic heart based on genetic information obtained by using the Yeast SST method described above. The mouse A55 clone is a full-length cDNA encoding a secreted polypeptide (which is called mouse A55 polypeptide here).

There was no DNA sequence identical to that of mouse and human A55 DNA sequence of the present invention when the DNA sequence of mouse A55 was compared with databases by BLASTN and FASTA. And there was no polypeptides identical to that of mouse and human A55 polypeptides of the present invention, when amino acid sequence of mouse and human A55 was compared with databases by BLASTX, BLASTP and FASTA. So the polypeptides of the present invention are considered to be novel.

The inventors discovered that the polypeptides had the ability to suppress smooth muscle cells. Accordingly, the polypeptides may be useful for treatment of diseases related to abnormal proliferation of smooth muscle cells, for example, arteriosclerotic coronary disease, neointimal formation which results in restenosis after percutaneous transluminal coronary angioplasty and myosarcoma.

The present invention provides:
1) a polypeptide comprising an amino acid sequence shown in SEQ ID NO: 3, 4, 8 or 9,
2) a cDNA encoding the polypeptide described above (1),
3) a cDNA having a nucleotide sequence shown in SEQ ID NO. 1, 5, 6 or 10, 4) a cDNA that consists of a nucleotide sequence shown in SEQ ID NO. 2 or 7.

BRIEF DESCRIPTION OF FIGURES

FIG. 1 shows that mouse A55 protein inhibits proliferation of rat aortic vascular smooth muscle cells which were stimulated by PDGF (platelet-derived growth factor).

DETAILED DESCRIPTION

Figure 1:
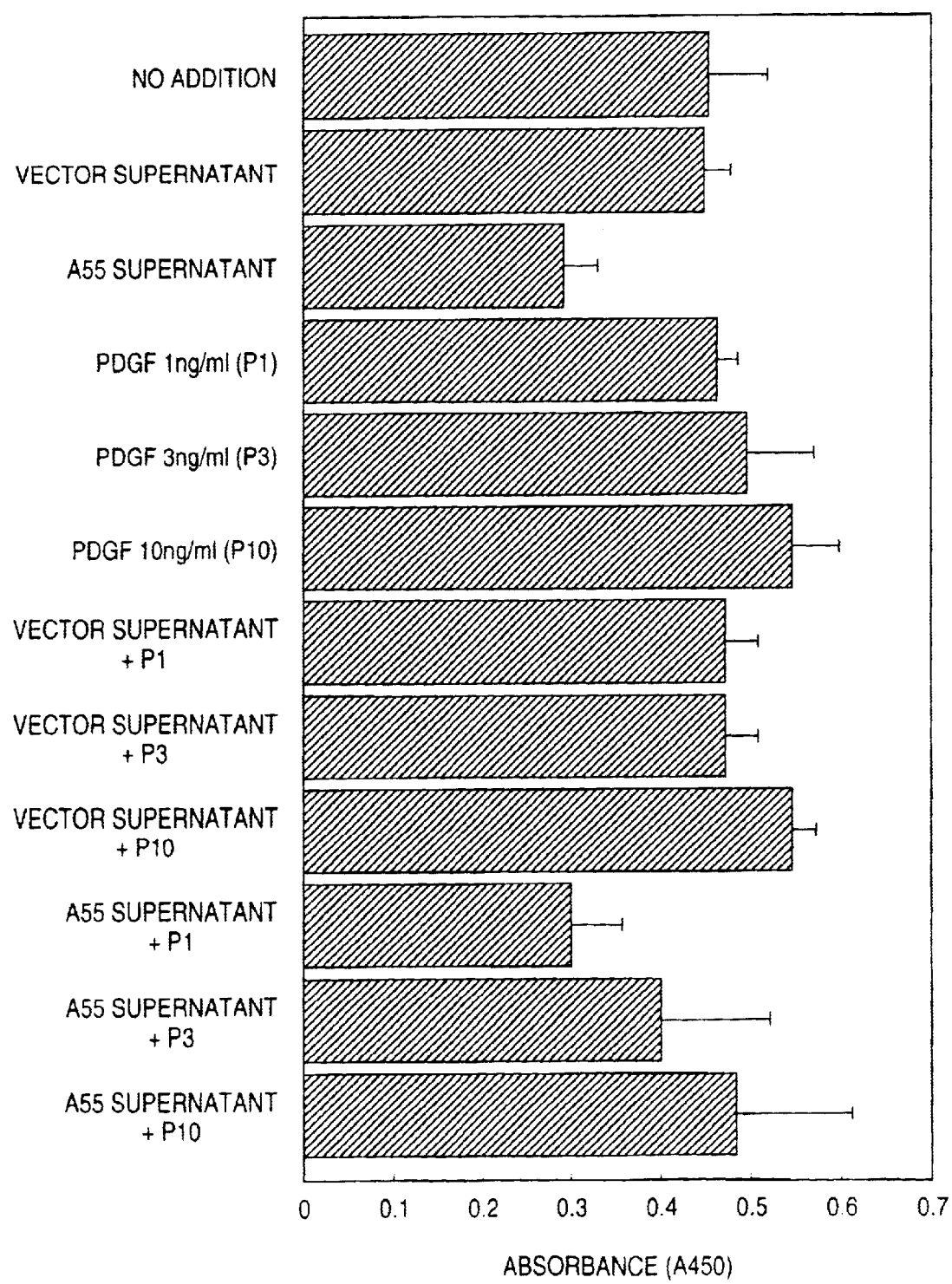
FIG. 1.

The present invention is concerned with a polypeptide that comprises the amino acid sequence shown in SEQ ID NO: 3, 4, 8 or 9 in substantially purified form a homologue thereof, a fragment of the sequence and a homologue of the fragment.

Further, the present invention is concerned with a cDNA encoding the above peptides. More particularly, the present invention provides a cDNA comprising the nucleotide sequence shown in SEQ ID NO: 1, 5, 6 or 10, and a cDNA containing a fragment which selectively hybridizes to the cDNA that comprises a nucleotide sequence shown in SEQ ID NO: 1, 5, 6 or 10. Complementary sequence of the above nucleotide sequence is also included in cDNA selectively hybridized. Hybridization is performed under stringent conditions.

A polypeptide comprising an amino acid sequence shown in SEQ ID NO: 3, 4, 8 or 9 in substantially purified form will generally comprise the polypeptide in a preparation in which more than 90%, e.g. 95%, 98% or 99% of the polypeptide in the preparation is that of the SEQ ID NO: 3, 4, 8 or 9.

A homologue of a polypeptide comprising an amino acid sequence shown in SEQ ID NO: 3, 4, 8 or 9 will be generally at least 70%, preferably at least 80 or 90% and more preferably at least 95% homologous to the polypeptide of SEQ ID NO: 3 over a region of at least 20, preferably at least 30, for instance 40, 60 or 100 more contiguous amino acids. Such a polypeptide homologue will be referred to as a polypeptide of the present invention.

Generally, a fragment of polypeptide comprising an amino acid sequence shown in SEQ ID NO: 3, 4, 8 or 9 or its homologues will be at least 10, preferably at least 15, for example 20, 25, 30, 40, 50 or 60 amino acids in length, and is also referred to by the term "a polypeptide of the present invention".

A cDNA capable of selectively hybridizing to the cDNA comprising a nucleotide sequence shown in SEQ ID NO: 1, 5, 6 or 10 will be generally at least 70%, preferably at least 80 or 90% and more preferably at least 95% homologous to the cDNA of SEQ ID NO: 1, 5, 6 or 10 over a region of at least 20, preferably at least 30, for instance 40, 60 or 100 or more contiguous nucleotides. Such cDNA will be referred to as "a cDNA of the present invention".

Fragments of the cDNA comprising nucleotide sequence shown in SEQ ID NO: 1, 5, 6 or 10 will be at least 10, preferably at least 15, for example 20, 25, 30 or 40 nucleotides in length, and will be also referred to as "a cDNA of the present invention" as used herein.

A further embodiment of the present invention provides replication and expression vectors carrying cDNA of the invention. The vectors may be, for example, plasmid, virus or phage vectors provided with an origin of replication, optionally a promoter for the expression of the said cDNA and optionally a regulator of the promoter. The vector may contain one or more selectable marker genes, for example an ampicillin resistance gene. The vector may be used in vitro, for example of the production of RNA corresponding to the cDNA, or used to transfect or transform a host cell.

A further embodiment of the present invention provides host cells transformed with the vectors for the replication and expression of the cDNA of the invention, including the nucleotide sequence shown in SEQ ID NO: 1, 2, 5, 6, 7 or 10 or the open reading frame thereof. The cells will be chosen to be compatible with the vector and may for example be bacterial, yeast, insect or mammalian.

A further embodiment of the present invention provides a method of producing a polypeptide which comprises culturing host cells of the present invention under conditions effective to express a polypeptide of the invention. Preferably, in addition, such a method is carried out under conditions in which the polypeptide of the invention is expressed and then produced from the host cells.

cDNA of the present invention may also be inserted into the vectors described above in an antisense orientation in order to provide for the production of antisense RNA. Such antisense RNA may be used in a method of controlling the levels of a polypeptide of the invention in a cell.

The invention also provides monoclonal or polyclonal antibodies against a polypeptide of the invention. The invention further provides a process for the production of monoclonal or polyclonal antibodies to the polypeptides of the invention. Monoclonal antibodies may be prepared by common hybridoma technology using polypeptides of the invention or fragments thereof, as an immunogen. Polyclonal antibodies may also be prepared by common means which comprise inoculating host animals, for example a rat or a rabbit, with polypeptides of the invention and recovering immune serum.

The present invention also provides pharmaceutical compositions containing a polypeptide of the invention, or an antibody thereof, in association with a pharmaceutically acceptable diluent and/or carrier.

The polypeptide of the present invention includes those in which a part of their amino acid sequence is lacking (e.g., a polypeptide comprised of only the essential sequence for revealing a biological activity in an amino acid sequence shown in SEQ ID NO: 3), those in which a part of their amino acid sequence is replaced by other amino acids (e.g., those replaced by an amino acid having a similar property) and those in which other amino acids are added or inserted into a part of their amino acid sequence, as well as those comprising the amino acid sequence shown in SEQ ID NO: 3, 4, 8 or 9.

As known well, there are between one and six different codons that encode each amino acid (for example, while only one codon specifies methionine (Met), there are six codons for leucine (Leu)). Accordingly, the nucleotide sequence of a cDNA can be changed in order to encode the polypeptide having the same amino acid sequence.

The DNA of the present invention, specified in (2) above, includes a group consisting of every nucleotide sequence encoding the polypeptides of (1) above, shown in SEQ ID NO: 3, 4, 8 or 9. There is a probability that the yield of a polypeptide is improved by changing the nucleotide sequence.

The cDNA specified in (3) above is an embodiment of the cDNA shown in (2), and is the sequence of the natural form.

The cDNA shown in (4) above is the sequence of the cDNA specified in (3) with the natural non-translated regions shown.

cDNA comprising the nucleotide sequence shown in SEQ ID NO: 2 or 7 is prepared by the following method:

A brief description of Yeast SST method (see U.S. Pat. No. 5,536,637) is as follows.

Yeast such as *Saccharomyces cerevisiae* should secrete invertase into the medium in order to utilize sucrose or raffinose as a source of energy or carbon. (Invertase is an enzyme that cleaves raffinose into sucrose and melibiose, and sucrose into fructose and glucose). It is known that many known mammalian signal peptides make yeast secrete its invertase. From this knowledge, the SST method was developed as a screening method to find novel signal peptides in a mammalian cDNA library which allow invertase secretion by yeast. SST method uses yeast growth on raffinose medium as a marker. Non-secretory type invertase gene SUC2 (GENBANK Accession No. V01311) lacking initiation codon ATG was inserted into a yeast expression vector to prepare the yeast SST vector pSUC2.

Into this expression vector, ADH promoter, ADH terminator (both were derived from AAH5 plasmid (Gammerer, *Methods in Enzymol.* 101, 192–201, 1983)), 2u ori (as a yeast replication origin). TRP1 (as a yeast selective marker), ColE1 ori (as a *E. coli* replication origin) and ampicillin resistance gene (as a drug resistance marker) were inserted. Mammalian cDNA was inserted into the upstream of the SUC2 gene to prepare a yeast SST cDNA library. Yeast lacking secretory type invertase were transformed with this library. If an inserted mammalian cDNA encodes a signal peptide, yeast could survive in raffinose medium as a result of restoring secretion of invertase. Only by culturing yeast colonies, preparing plasmids and determine the nucleotide sequence of the insert cDNAs, is it possible to identify novel signal peptides rapidly and easily.

Preparation of a yeast SST cDNA library is as follows:

(1) mRNA is isolated from the targeted cells, second-strand synthesis is performed by using a random primer containing a particular restriction enzyme (enzyme I) recognition site, (2) double-strand cDNA is ligated to an adapter containing a particular restriction endonuclease (enzyme II) recognition site that differs from enzyme I, then digested with enzyme I and fractionated in a appropriate size, (3) obtained cDNA fragments are inserted into yeast expression vector in the upstream region of the invertase gene having the signal peptide deleted, and the library is transformed.

Detailed description of each step is as follows:

In step (1), mRNA is isolated from mammalian organs and cell lines (stimulated with an appropriate stimulator if necessary) by known methods (*Molecular Cloning* (Sambrook, J., Fritsch, E. F. and Maniatis, T., Cold Spring Harbor Laboratory Press, 1989) or *Current Protocol in Molecular Biology* (F. M. Ausubel et al, John Wiley & Sons, Inc.) if not remark especially).

Mouse embryonic heart is chosen as a tissue source. Double-strand cDNA synthesis using a random primer is performed by known methods.

Any sites may be used as restriction endonuclease recognition site I which is linked to an adapter and restriction endonuclease recognition site II which is used in step (2), as long as both sites are different from each other. Preferably, XhoI is used as enzyme I and EcoRI as enzyme II.

In step (2), cDNA is blunt-ended with T4 DNA polymerase, ligated to the enzyme II adapter and digested with enzyme I. Fragment cDNA is analyzed with agarose-gel electrophoresis and a cDNA fraction ranging in size from 300 to 800 bp is selected. As mentioned above, any enzyme may be used as enzyme II as long as it is not same the enzyme I.

In step (3), cDNA fragments obtained in step (2) are inserted into the yeast expression vector in the upstream region of the invertase gene in which the signal peptide has been deleted. *E. coli* are then transformed with the expression vector. Many vectors are known as yeast expression plasmid vectors. For example, YEp24 is also functional in *E. coli*. Preferably pSUC2 as described above is used.

Many host *E. coli* strains are known for use in transformation, preferably DH10B competent cells are used. Any known transformation method is may be used, but preferably transformation is performed using an electroporation method. Transformants are cultured by known methods to obtain a cDNA library for use in the yeast SST method.

However not all of the clones will contain cDNA fragments. Further, not all of the gene fragments will encode unknown signal peptides. It is therefore necessary to screen for gene fragments that encode an unknown signal peptide from the library.

Screening of fragments containing a sequence encoding an appropriate signal peptide is performed by transformation of the cDNA library into *Saccharomyces cerevisiae* (e.g. YT455 strain) which lacks invertase (it may be prepared by known methods). Transformation of yeast is performed by known methods, e.g. the lithium acetate method. Transformants are cultured in a selective medium, then transferred to a medium containing raffinose as a carbon source. Surviving colonies are selected and plasmids are isolated therefrom. Surviving colonies on a raffinose-medium indicates that a signal peptide of a secretory protein has been inserted into the surviving clone.

The nucleotide sequence of isolated positive clones is determined. As to a cDNA encoding an unknown protein, a full-length clone may be isolated by using a cDNA fragment as a probe and obtaining the full-length nucleotide sequence. These manipulation are performed by known methods.

Once the nucleotide sequences shown in SEQ ID NO: 1, 5, 6 or 10 are determined partially or preferably fully, it is possible to obtain a cDNA encoding the mammalian protein itself, and a homologue or subset of the invention.

A cDNA library or mRNA derived from mammals was screened by PCR with any synthesized oligonucleotide primer or by hybridization with any fragment as a probe. It is possible to obtain cDNA encoding other mammalian homologue proteins from another mammalian cDNA or genome library.

If a cDNA obtained above contains a nucleotide sequence of a cDNA fragment obtained by SST (or consensus sequence thereof), it will be thought that the cDNA encodes a signal peptide. So it is clear that the cDNA will be full-length or almost full. (All signal peptides exist at N-termini of a protein and arc encoded at the 5'-termini of the open reading frame of the cDNA.)

The confirmation may be carried out by Northern analysis with the cDNA as a probe. It is thought that the cDNA is almost of complete length, if the length of the cDNA is almost the same length of the mRNA obtained in the hybridizing band.

The present invention supplies full-length proteins and their mature protein sequences. The full-length protein sequence is deduced from nucleotide sequences shown in SEQ ID NO: 1 or 6. Mature proteins are obtained by expressing full-length cDNAs shown in SEQ ID NO: 2 or 7 in mammalian cells or other host cells. Mature protein sequences are deduced from their full-length amino acid sequences.

Once the nucleotide sequences shown in SEQ ID NOs: 1, 5, 6 or 10 are determined, cDNAs of the present invention are obtained by chemical synthesis, or by hybridization making use of nucleotide fragments which are chemically synthesized as probes. Furthermore, cDNAs of the present invention are obtained in desired amounts by transforming a vector that contains the cDNA into a proper host, and culturing the transformant.

The polypeptides of the present invention may be prepared by:

(1) isolation and purification from an organism or a cultured cell, (2) chemical synthesis, or (3) using recombinant DNA technology, preferably, by the method described in (3) in industrial production.

Examples of expression systems (host-vector systems) for producing a polypeptide by using recombinant DNA technology are the expression systems of bacteria, yeast, insect cells and mammalian cells.

In the expression of the polypeptide, for example in *E. coli*, the expression vector is prepared by adding the initiation codon (ATG) to 5' end of a DNA encoding the mature peptide, connecting the DNA thus obtained to the downstream end of a proper promoter (e.g., trp promoter, lac promoter, λ PL promoter, T7 promoter etc.), and then inserting it into a vector (e.g., pBR322, pUC18, pUC19 etc.) which functions in an *E. coli* strain.

Then, an *E. coli* strain (e.g., *E. coli* DH1 strain, *E. coli* JM109 strain, *E. coli* HB101 strain. etc.) which is transformed with the expression vector described above may be cultured in an appropriate medium to obtain the desired polypeptide. When a bacterial signal peptide (e.g., signal peptide of pel B) is utilized, the desired polypeptide may be also released into the periplasm. Furthermore, a fusion protein with another polypeptide may be also produced easily.

In the expression of the polypeptide, for example in a mammalian cells, the expression vector is prepared by inserting the DNA shown in SEQ ID NO: 1, 5, 6 or 10 downstream of a proper promoter (e.g., SV40 promoter, LTR promoter, metallothionein promoter etc.) in a proper vector (e.g., retrovirus vector, papilloma virus vector, vaccinia virus vector, SV40 vector, etc.). A proper mammalian cell (e.g., monkey COS-7 cell, Chinese hamster CHO cell, mouse L cell etc.) is then transformed with the expression vector thus obtained, and then the transformant is cultured in a proper medium to get a desired polypeptide in the culture medium. Further, a fusion protein may be produced by linking a cDNA fragment encoding another polypeptide such as the Fc portion of an antibody. The polypeptide thus obtained may be isolated and purified by conventional biochemical methods.

Industrial Utility

The polypeptides of the present invention and cDNA encoding them are expected to exhibit one or more of the uses or biological activities (including those associated with assays cited herein) identified below.

Uses or activities described for proteins of the present invention may be provided by administration or use of such proteins or by administration or use of cDNA encoding them (such as, for example, in gene therapies or vectors suitable for introduction of DNA).

We have confirmed that the polypeptide possesses suppressing activity on the differentiation of vascular smooth muscle cells. Accordingly, the polypeptides may be useful for treatment of diseases related to abnormal proliferation of smooth muscle cells, for example, arteriosclerotic coronary disease, neointimal formation which results in restenosis after percutaneous transluminal coronary angioplasty, and myosarcoma.

But not to limit the present invention, the inventors note that the present polypeptide may show the following activity.

Cytokine Activity and Cell Proliferation/differentiation Activity

The protein of the present invention may exhibit cytokine, cell proliferation (either inducing or inhibiting) or cell differentiation (either inducing or inhibiting) activity or may induce production of other cytokines in certain cell populations.

Many protein factors discovered to date, including all known cytokines, have exhibited activity in one or more factor-dependent cell proliferation assays, and hence the assays serve as a convenient confirmation of cytokine activity.

The activity of a protein of the present invention is evidenced by any one of a number of routine factor-dependent cell proliferation assays for cell lines.

Immune Stimulating/suppressing Activity

The protein of the present invention may also exhibit immune stimulating or immune suppressing activity. The protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations.

These immune deficiencies may be genetic or be caused by viral (e.g. HIV) as well as bacterial or fungal infections, or may result from autoimmune disorders.

More specifically, infectious diseases caused by viral, bacterial, fungal or other infection may be treatable using the protein of the present invention, including infections by HIV, hepatitis viruses, herpes viruses, mycobacteria, leshmania, malaria and various fungal infections such as candida. Of course, in this regard, a protein of the present invention may also be useful where a boost to the immune system generally would be indicated, i.e., in the treatment of cancer.

Such a protein of the present invention may also be useful in the treatment of allergic reactions and conditions, such as asthma or other respiratory problems.

The protein of the present invention may also suppress chronic or acute inflammation, such as, for example, that associated with infection (such as septic shock or systemic inflammatory response syndrome (SIRS)), inflammatory bowel disease, Crohn's disease or resulting from over production of cytokines such as TNF or IL-I (such as the effect demonstrated by IL-11).

Hematopoiesis Regulating Activity

The protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis.

The biological activities are concerned with one or more of the following examples: in supporting the growth and proliferation of erythroid progenitor cells alone or in combination with other cytokines, in treating various anemias or for use in conjunction with irradiation/chemotherapy to stimulate the production of erythroid precursors and/or erythroid cells; in supporting the growth and proliferation of myeloid cells such as granulocytes and monocytes/ macrophages (i.e., traditional CSF activity) useful, for example, in conjunction with chemotherapy to prevent or treat consequent myelo-suppression; in supporting the growth and proliferation of megakaryocytes, and consequently of platelets, thereby allowing prevention or treatment of various platelet disorders such as thrombocytopenia, and generally for use in place of or complimentary to platelet transfusions; and in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e. in conjunction with bone marrow transplantation) as normal cells or genetically manipulated for gene therapy, thereby indicating utility.

Suitable assays for proliferation and differentiation of various hematopoietic lines are cited above.

The activity of a protein of the invention may, among other means, be measured by the following methods.

Tissue Generation/regeneration Activity

The protein of the present invention also may have utility in compositions used for bone, cartilage, tendon, ligament and/or nerve tissue growth or regeneration, as well as for wound healing and tissue repair, and in the treatment of burns, incisions and ulcers.

The protein of the present invention, which induces cartilage and/or bone growth in circumstances where bone is not normally formed, has application in the healing of bone fractures and cartilage damage or defects in humans and other animals. Such a preparation employing the protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

The protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. The protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments.

The compositions of the present invention may provide an environment to attract tendon- or ligament-forming cells, stimulate growth of tendon- or ligament-forming cells, induce differentiation of progenitors of tendon- or ligament-forming cells, or induce growth of tendon or ligament cells or progenitors ex vivo for return in vivo to effect tissue repair.

The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e., for the treatment of central and peripheral nervous system diseases and neuropathies as well as mechanical and traumatic disorders, which involve degeneration, death or trauma to neural cells or nerve tissue.

More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome.

Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

It is expected that the protein of the present invention may also exhibit activity for generation of other tissues, such as organs (including, for example, pancreas, liver, intestine, kidney, skin, endothelium), muscle (smooth, skeletal or cardiac) and vascular (including vascular endothelium) tissue, or for promoting or suppressing the proliferation of cells comprising such tissues. Part of the desired effects may be by inhibition of fibrotic scarring to allow normal tissue to regenerate.

A protein of the present invention may also be useful for gut protection or regeneration and treatment of lung or liver fibrosis, reperfusion injury in various tissues, and conditions resulting from systemic cytokine damage.

Activin/inhibin Activity

The protein of the present invention may also exhibit activin- or inhibin-related activities. Inhibins are characterized by their ability to inhibit the release of follicle stimulating hormone (FSH), while activins are characterized by their ability to stimulate the release of follicle stimulating hormone (FSH).

Thus, a protein of the present invention, alone or in heterodimers with a member of the inhibin *a family, may be useful as a contraceptive based on the ability of inhibins to decrease fertility in female mammals and decrease spermatogenesis in male mammals. Administration of sufficient amounts of other inhibins can induce infertility in these mammals.

Alternatively, the protein of the invention, as a homodimer or as a heterodimer with other protein subunits of the inhibin-*b group, may be useful as a fertility-inducing therapeutic, based upon the ability of activin molecules in stimulating FSH release from cells of the anterior pituitary. See, for example, U.S. Pat. No. 4,798,885. The polypeptide of the invention may also be useful for advancement of the onset of fertility in sexually immature mammals, so as to increase the lifetime reproductive performance of domestic animals such as cows, sheep and pigs.

Chemotactic/chemokinetic Activity

A protein of the present invention may have chemotactic or chemokinetic activity (e.g., act as a chemokine) for mammalian cells, including, for example, monocytes, neutrophils, T-cells, mast cells, eosinophils and/or endothelial cells.

Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

Hemostatic and Thrombolytic Activity

The protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction or stroke).

Receptor/ligand Activity

The protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including, without limitation, cellular adhesion molecules (such as selectins, integrins and their ligands) and receptor/ligand pairs involved in antigen presentation, antigen recognition and development of cellular and humoral immune responses).

Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

Nutritional Uses

Proteins of the present invention can also be used as nutritional sources or supplements. Such uses include, without limitation, use as a protein or amino acid supplement, use as a carbon source, use as a nitrogen source and use as a source of carbohydrate. In such cases, the protein of the present invention can be added to the feed of a particular organism or can be administered as a separate solid or liquid preparation, such as in the form of powder, pills, solutions, suspensions or capsules. In the case of microorganisms, the protein of the invention can be added to the medium in or on which the microorganism is cultured.

Cadherin/tumor Invasion Suppresser Activity

Cadherins are calcium-dependent adhesion molecules that appear to play major roles during development, particularly in defining specific cell types. Loss or alteration of normal cadherin expression can lead to changes in cell adhesion properties linked to tumor growth and metastasis. Cadherin malfunction is also implicated in other human diseases, such as pemphigus vulgaris and pemphigus foliaceus (autoimmune blistering skin diseases), Crohn's disease, and some developmental abnormalities.

The cadherin superfamily includes well over forty members, each with a distinct pattern of expression. All members of the superfamily have in common conserved extracellular repeats (cadherin domains), but structural differences are found in other parts of the molecule. The cadherin domains bind calcium to form their tertiary structure and thus calcium is required to mediate their adhesion. Only a few amino acids in the first cadherin domain provide the basis for homophilic adhesion; modification of this recognition site can change the specificity of a cadherin so that instead of recognizing only itself, the mutant molecule can now also bind to a different cadherin. In addition, some cadherins engage in heterophilic adhesion with other cadherin.

E-cadherin, one member of the cadherin superfamily, is expressed in epithelial cell types. Pathologically, if E-cadherin expression is lost in a tumor, the malignant cells become invasive and the cancer metastasizes. Transfection of cancer cell line with cDNAs expressing E-cadherin has reversed cancer-associated changes by returning altered cell shapes to normal, restoring cells adhesiveness to each other and to their substrate, decreasing the cell growth rate, and drastically reducing anchorage-independent cell growth.

Thus, reintroducing E-cadherin expression reverts carcinomas to a less advanced stage. It is likely that other cadherins have the same invasion suppresser role in carcinomas derived from other tissue types. Therefore, proteins of the present invention with cadherin activity, and cDNAs of the present invention encoding such proteins, can be used to treat cancer. Introducing such proteins or cDNAs into cancer cells can reduce or eliminate the cancerous change observed in these cells by providing normal cadherin expression.

Cancer cells have also been shown to express cadherins of a different tissue type than their origin, thus allowing these cells to invade and metastasize in a different tissue in the body. Proteins of the present invention with cadherin activity, and cDNAs of the present invention encoding such proteins, can be substituted in these cells for the inappropriately expressed cadherins, restoring normal cell adhesive properties and reducing or eliminating the tendency of the cells to metastasize.

Additionally, proteins of the present invention with cadherin activity, and cDNA of the present invention encoding such proteins, can be used to generate antibodies recognizing and binding to cadherins. Such antibodies can be used to block the adhesion of inappropriately expressed tumor-cell cadherins, preventing the cells from forming a tumor elsewhere. Such an anti-cadherin antibody can also be used as a marker for the grade, pathological type, and prognosis of a cancer, i.e. the more progressed the cancer, the less cadherin expression there will be, and this decrease in cadherin expression can be detected by the use of a cadherin-binding antibody.

Fragments of proteins of the present invention with cadherin activity, preferably a polypeptide comprising a decapeptide of the cadherin recognition site, and cDNAs of the present invention encoding such protein fragments, can also be used to block cadherin function by binding to cadherins and preventing them from binding in ways that produce undesirable effects.

Additionally, fragments of proteins of the present invention with cadherin activity, preferably truncated soluble cadherin fragments which have been found to be stable in the circulation of cancer patients, and polynucleotides encoding such protein fragments, can be used to disturb proper cell-cell adhesion.

Tumor Inhibiting Activity

In addition to the activities described above for immunological treatment or prevention of tumors, the protein of the invention may exhibit other anti-tumor activities. The protein may inhibit tumor growth directly or indirectly (such as, for example, via ADCC). The protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activity

The protein of the invention may also exhibit one or more of the following additional activities or effects: inhibiting the growth, infection or function of, or killing, infectious agents, including, bacteria, viruses, fungi and other parasites; effecting (suppressing or enhancing) bodily characteristics, including, height, weight, hair color, eye color, skin, fat to lean ratio or other tissue pigmentation, or organ or body part size or shape (such as, for example, breast augmentation or diminution); effecting elimination of dietary fat, protein, carbohydrate; effecting behavioral characteristics, including appetite, libido, stress, cognition (including cognitive disorders), depression and violent behaviors; providing analgesic effects or other pain reducing effects; promoting differentiation and growth of embryonic stem cells in lineages other than hematopoietic lineages; and in the case of enzymes, correcting deficiencies of the enzyme and treating deficiency-related diseases.

The polypeptide with the above activities, is suspected to have the following functions by itself or due to interaction with its ligands or receptors or association with other molecules. For example, proliferation or cell death of B cells, T cells and/or mast cells or class specific induction of B cells by promotion of class switch of immunoglobulin genes; differentiation of B cells to antibody-forming cells; proliferation, differentiation, or cell death of precursors of granulocytes; proliferation, differentiation, or cell death of precursors of monocytes-macrophages; proliferation, up-regulation or cell death of neutrophils, monocytes-macrophages, eosinophils and/or basophils; proliferation, or cell death of precursors of megakaryocytes; proliferation, differentiation, or cell death of precursors of neutrophils; proliferation, differentiation, or cell death of precursors of T cells and B cells; promotion of production of erythrocytes; sustainment of proliferation of erythrocytes, neutrophils, eosinophils, basophils, monocytes-macrophages, mast cells, precursors of megakaryocyte; promotion of migration of neutrophils, monocytes-macrophages, B cells and/or T cells; proliferation or cell death of thymocytes; suppression of differentiation of adipocytes; proliferation or cell death of natural killer cells; proliferation or cell death of hematopoietic stem cells; suppression of proliferation of stem cells and each hematopoietic precursor cells; promotion of differentiation from mesenchymal stem cells to osteoblasts or chondrocytes, proliferation or cell death of mesenchymal stem cells, osteoblasts or chondrocytes and promotion of bone absorption by activation of osteoclasts and promotion of differentiation from monocytes to osteoclasts.

This peptide is also suspected to function to nervous system, so expected to have functions below; differentiation to kinds of neurotransmitter-responsive neurons, survival or cell death of these cells; promotion of proliferation or cell death of glial cells; spread of neural dendrites; survival or cell death of gangliocytes; proliferation, promotion of differentiation, or cell death of astrocytes; proliferation or survival of peripheral neurons; proliferation or cell death of Schwann cells; proliferation, survival or cell death of motoneurons.

Furthermore, in the process of development of early embryos, this polypeptide is expected to promote or inhibit the organogenesis of epidermis, brain, backbone, and nervous system by induction of ectoderm, that of notochord connective tissues (bone, muscle, tendon), hemocytes, heart, kidney, and genital organs by induction of mesoderm, and that of digestive apparatus (stomach, intestine, liver, pancreas), respiratory apparatus (lung, trachea) by induction of endoderm. In adult, also, this polypeptide is thought to proliferate or inhibit the above organs.

Therefore, this polypeptide itself is expected to be used as an agent for the prevention or treatment of disease of progression or suppression of immune, nervous, or bone metabolic function, hypoplasia or overgrowth of hematopoietic cells: inflammatory disease (rheumatism, ulcerative colitis, etc.), decrease of hematopoietic stem cells after bone marrow transplantation, decrease of leukocytes, platelets, B-cells, or T-cells after radiation exposure or chemotherapeutic dosage against cancer or leukemia, anemia, infectious disease, cancer, leukemia, AIDS, bone metabolic disease (osteoporosis etc.), arteriosclerosis, various degenerative disease (Alzheimer's disease, multiple sclerosis, etc.), or nervous lesion.

In addition, since this polypeptide is thought to induce the differentiation or growth of organs derived from ectoderm, mesoderm, and endoderm, this polypeptide is expected to be an agent for tissue repair (epidermis, bone, muscle, tendon, heart, kidney, stomach, intestine, liver, pancreas, lung, and trachea, etc.).

Quantititation of this polypeptide in the body can be performed using polyclonal or monoclonal antibodies against this polypeptide. It can be used in the study of the relationship between this polypeptide and disease or diagnosis of disease, and so on. Polyclonal and monoclonal antibodies can be prepared using this polypeptide or its fragment as an antigen by known methods.

Identification, purification or molecular cloning of known or unknown proteins which bind this polypeptide can be performed using this polypeptide by, for example, preparation of an affinity-column.

Identification of the molecules which interact with this polypeptide and molecular cloning of the gene can be performed by west-western method using this polypeptide or by yeast two-hybrid system using the cDNA (preferably cDNA encoding this polypeptide).

Agonists/antagonists of this receptor polypeptide and inhibitors between receptor and signal transduction molecules can be screened using this polypeptide.

For example, the screening can be carried out by the following method.

a) The reaction mixtures, which contain this polypeptide, screening compound and the cells, are incubated under the conditions in which the cells are normally stimulated by this peptide. The reaction mixtures also contain the labeled compound, which is introduced into the cells according to the cell proliferation, and which allows the observation of the function of this peptide efficiently.

b) Analyses to determine whether the compounds are efficient agonists/antagonists are performed by measurement of cell proliferation ability.

More detailed methods are as follows.

A Rat vascular muscle cell line (ATCC CRL-1444 or CRL1476) is cultured in a 96 well plate with 10% FBS for 24 hours. Then the culture medium is replaced with serum-free medium supplemented with each of several concentrations of human PDGF-BB. At that time compounds to be screened, as well as A55 protein, are added in the medium when screening of the antagonists of A55 protein is to be performed. Compounds to be screened are added alone in the medium when screening for agonists of A55 protein. After 24 hours incubation, these cells are pulsed for 4 hours with 3H-thymidine. By measuring the 3H-thymidine incorporation, it is possible to determine whether the compounds have inhibitory or stimulatory effect on the A55 activity.

cDNAs of the present invention are useful not only the important and essential template for the production of the polypeptide of the present invention which is expected to be largely useful, but are also useful for diagnosis or therapy (for example, treatment of gene deficiency, treatment to stop the expression of the polypeptide by antisense DNA (RNA)).

Genomic DNA may be isolated by using the cDNA of the present invention as a probe. In the same manner, a mouse or human gene encoding a gene highly homologous to the cDNA of the present invention, that in turn encodes a polypeptide highly homologous to the polypeptide of the present invention, and a gene of an animal other than mouse or human that is also highly homologous to the cDNA of the present invention, may be isolated.

Application for Pharmaceuticals

For the medical treatment for diseases described above, the polypeptide of the invention or the antibody of the polypeptide of the invention may be administered systemically or partially in most cases, usually by oral or parenteral administration, preferably orally, intravenously or intraventricularly.

The doses to be administered depend upon age, body weight, symptom, desired therapeutic effect, route of administration, and duration of the treatment etc. In human adults, one dose per person is generally between 100 µg and 100 mg, by oral administration, up to several times per day, and between 10 µg and 100 mg, by parenteral administration up to several times per day.

As mentioned above, the doses to be used depend upon various conditions. Therefore, there are cases in which doses lower than or greater than the ranges specified above may be used.

The compounds of the present invention may be administered as solid compositions, liquid compositions or other compositions for oral administration, and as injections, liniments or suppositories etc. for parenteral administration.

Solid compositions for oral administration include compressed tablets, pills, capsules, dispersible powders, and granules. Capsules include soft or hard capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents, e.g., lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid, etc.).

The tablets or pills may, if desired, be coated with a film of gastric or enteric materials (such as sugar, gelatin, hydroxypropyl cellulose or hydroxypropylmethyl cellulose phthalate, etc.), or be coated with more than two films. And then, coating may include containment within capsules of absorbable materials such as gelatin.

Liquid compositions for oral administration include pharmaceutically-acceptable emulsions, solutions, syrups and elixirs. In such compositions, one or more of the active compound(s) is or are contained in inert diluent(s) commonly used (purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents, e.g., stabilizing agents (sodium sulfite etc.), and isotonic buffer (sodium chloride, sodium citrate, citric acid, etc.). For preparation of such spray compositions, for example, the method described in the U.S. Pat. Nos. 2,868,691 or 3,095,355 (herein incorporated in their entireties by reference) may be used.

Injections for parenteral administration include sterile aqueous or non-aqueous solutions, suspensions and emulsions. In such compositions, one or more active compound(s) is or are admixed with at least one inert aqueous diluent(s) (distilled water for injection, physiological salt solution, etc.) or inert non-aqueous diluents(s) (propylene glycol, polyethylene glycol, olive oil, ethanol, POLYSORBATE 80™, etc.).

Injections may comprise additional compound other than inert diluents: e.g. preserving agents, wetting agents, emulsifying agents, dispersing agents, stabilizing agent (such as human serum albumin, lactose, etc.), and assisting agents such as assisting agents for dissolving (arginine, asparaginic acid, etc.).

The Best Mode of the Invention

The following examples concerning clone A55 are illustrated, but do not limit the present invention.

EXAMPLE 1

Preparation of Poly(A)+RNA

Total RNA was prepared from mouse day 18.5 embryonic heart by TRIzol™ reagent (Trade Mark, GIBCOBRL), and poly (A)$^+$ RNA was purified from the total RNA by mRNA Purification Kit™ (Trade Mark, Pharmacia).

EXAMPLE 2

Preparation of Yeast SST cDNA Library

Double strand cDNA was synthesized by SuperScript™ Plasmid System for cDNA Synthesis and Plasmid Cloning (brand name, GIBCOBRL) with the above poly(A)+RNA as the template and a random 9-meras primer that also contained an XhoI site:

5'-CGA TTG AAT TCT AGA CCT GCC TCG AGN NNN NNN NN-3' (SEQ ID NO: 11)

To the cDNA was then ligated a EcoRI adapter by DNA ligation kit ver 2 (trade name, Takara Shuzo; this kit was used in all ligating steps hereafter) and the mixture was then digested by XhoI. The cDNAs were separated by agarose-gel electrophoresis, 300–800 bp cDNAs were isolated and the isolated cDNAs were ligated into the EcoRI/NotI site of pSUC2 (see U.S. Pat. No. 5.536.637). *E. coli* DH10B strain were transformed by pSUC2 using electroporation to obtain a yeast SST cDNA library.

EXAMPLE 3

Screening by SST Method and DNA Sequencing of Positive Clones

Plasmids of the cDNA library were prepared. Yeast YTK12 strain was transformed by the plasmids using the lithium acetate method (Current Protocols In Molecular Biology, 13.7.1). The transformed yeast were plated on tryptophan-free medium (CMD-Try medium) for selection. The plate were incubated for 48 hour at 30° C. Replicas of colonies which were obtained were replica plated by Accu-tran Replica Plater (trade name, Schleicher & Schuell) to YPR plates containing raffinose as carbon source and incubated for 14 days at 30° C.

After 3 days, each colony that appeared was streaked onto a fresh YPR plate. The plates were incubated for 48 hours at 30° C. Single colonies were inoculated to YPR medium and were incubated for 48 hours at 30° C. Then plasmids were prepared from the isolated colonies. Insert cDNA was amplified by PCR using two kind primers complementary to 5' and 3' ends of the cloning site on pSUC2 (sense strand primers were biotinylated). Biotinylated single strands of cDNAs were purified with Dynabeads (trade name, DYNAL) and the nucleotide sequences were determined.

Sequencing was performed by Dye Terminator Cycle Sequencing Ready Reaction with DNA Sequencing kit (trade name, Applied Biosystems Inc.) and the sequence was determined using a DNA sequencer 373 (Applied Biosystems Inc.). All sequencing hereafter was carried out by this method.

The clone named A55 did not registered on databases by homology search of cDNA sequence and deduced amino acid sequence and so it was clear that the sequence was a novel one. Next, isolation and cloning of full-length cDNA using the fragment of the A55 clone (hereafter A55 SST fragment cDNA) was attempted. It was confirmed that the A55 SST fragment cDNA contains a signal peptide by comparison with known peptides which have signal peptides in view of function and structure.

EXAMPLE 4

Cloning and Sequencing of a Full-length cDNA of A55

Phage particles of a cDNA library of mouse day 13 embryonic heart(uni-ZAP XR, Stratagene) were transfected into *E. coli* XL1-Blue MRF* host cells (Stratagene). One million plaques were obtained and transferred to nylon membranes. The membranes were hybridized with 32P-labeled mouse A55 SST fragment cDNA as a probe. Many positive plaques were obtained.

From one positive plaque, the phage particles containing a cloned insert were prepared, and were subjected to conversion into phagemid particles (pBluescript SK(–)) by co-infection of *E. coli* XL1-Blue MRF* host cells (Stratagene) with ExAssist helper phage (Stratagene). The phagemid particles were transfected to *E. coli* DH5a. The plasmids were prepared from the ,obtained transformants.

Nucleotide sequence of the 5'-end of the cDNA were determined to confirm the existence of the sequences of the SST fragment cDNA. Full-length sequencing was then performed to obtain a cDNA encoding SEQ ID NO:3.

An open reading franie was determined. The translation region of coding DNA sequence for the amino acid sequence is shown in SEQ ID NO: 1 and the deduced full-length amino acid sequence is shown in SEQ ID NO: 3. A mature version of the protein was deduced to be 425 amino acids, as encoded by SEQ ID NO: 2 (144 . . . 1418) or 423 amino acids as shown in SEQ ID NO. 4. The translated region of SEQ ID NO. 4 is shown in SEQ ID NO.5.

TABLE I

| | |
|---|---|
| Coding sequence of clone A55 | SEQ ID NO: 1 |
| Coding sequence of clone A55 with 5' and 3' untranslated regions | SEQ ID NO: 2 |
| Full-length amino acid sequence of clone A55 | SEQ ID NO: 3 |
| Amino acid sequence of clone A55, minus signal peptide and first two amino acids of the mature protein | SEQ ID NO: 4 |
| Nucleic acid sequence of truncated protein of SEQ ID NO: 4 | SEQ ID NO: 5 |
| Coding sequence of clone A55b | SEQ ID NO: 6 |
| Coding sequence of clone A55b with 5' and 3' untranslated regions | SEQ ID NO: 7 |
| Full-length amino acid sequence of clone A55b | SEQ ID NO: 8 |
| Amino acid sequence of clone A55b, minus signal peptide and first two amino acids of the mature protein | SEQ ID NO: 9 |
| Nucleic acid sequence of truncated protein of SEQ ID NO: 9 | SEQ ID NO: 10 |

It was confirmed that there was no identical sequences to the DNA of the present invention by homology search programs program, BLASTN and FASTA, against public nucleotide databases. And it was also confirmed that there were no identical sequences to the polypeptide of the present invention (mouse A55 protein) by homologue search programs, BLASTX, BLASTP and FASTA, against amino acid databases.

It is revealed that the polypeptide of the present invention, mouse A55 protein, is a novel secretion protein since the polypeptide have no trans-membrane region by hydrophobicity analysis of the amino acid sequence.

It was revealed that A55 protein contained six EGF-like domains by motif search, so it was expected that clone A55 also possesses EGF family-like activities. Significant homology was also recognized between the amino acid sequence of mouse A55 clone (1–448 AA region) and the one of human S1–5 (SwissProt Accession No. HSU03877) (1–387 AA region) by comparison using BLASTX, BLASTP and FASTA. It was reported that human S1–5 was a secreted protein containing an EGF-like domain, was induced in fibroblasts by growth arrest, and stimulated DNA synthesis (Beata Lecka-Czernik et. al. Mol. Cell. Biol. 15, 120–128, 1995). Further, it was revealed that the A55 protein was homologous to many proteins containing an EGF-like domain.

EXAMPLE 5

Isolation of an Isoform Gene of Mouse A55 Protein

Initiation codon was determined by the cloning of the 5'-end cDNA by 5'-RACE (Rapid Amplification of cDNA Ends method, using Marathon cDNA Amplification Kit (trade name, Clontech).

Double stranded cDNA template was prepared from poly (A)+RNA of mouse embryonic heart tissue. Primer mA55-R1:

5'-CGT TTG TGC ACT GCT GCT GTG CAT TCC -3' (SEQ ID NO: 12)

was prepared based on the information of full-length nucleotide sequences. PCR was performed with the primer and adapter primer included in the kit.

Amplified cDNA was separated with agarose-gel electrophoresis, ligated into pGEM-T Vector (trade name, Promega), and transformed into *E. coli* DH5a, and then plasmid were prepared. The full-length nucleotide sequences were determined. Two different 5'-end sequences were found. One was identical to the clone containing the sequence in SEQ ID NO: 2, the other contained an unknown sequence and no translational start site ATG.

That the region defined by exon 1 of the A55 clone was replaced by another exon which exists 400 bp downstream from the region of A55 exon1 was clarified by gene analysis. So it was thus clear that the clone shown in SEQ ID NO: 7 was generated by alternative splicing of exon 1. This latter clone encodes an isoform protein (A55b) shown in SEQ ID NO: 8 (due to alternative splicing, the first 6 amino acids in the N-termini of the A55 protein of SEQ ID NO: 3 were replaced by the first 19 amino acids found in the N-termini of the A55b protein of SEQ ID NO: 8).

The mature protein of this polypeptide was deduced to be 425 amino acids, as can be seen in SEQ ID NO: 7 (340 . . . 1614) or 423 amino acids as shown in SEQ ID NO. 9. SEQ ID NO. 10 is an amino acid to nucleic acid translation of the polypeptide shown in SEQ ID NO. 9.

EXAMPLE 6

Mouse A55 Protein Expression in Mammalian Cell

Mouse full-length cDNA shown in SEQ ID NO: 2 was inserted into the mammalian cell expression vector pNotS (Kaufman et al., Nucleic Acids Res. 19, 4485–4490 (1991)) and mouse A55 expression plasmid pNotS-mA55 was constructed.

293T cells (which are derived from 293 cells (ATCC CRL-1573) and are stably transfected with SV40 T antigen) were transfected with pNotS and pNotS-mA55 using lipofection (GIBCOBRL). After preincubated for 19 hours, the cells were pulsed for 30 minutes with $^{35}$S-Met in the Met-free medium. Then the cells were incubated in the medium containing Met for 5 hours. Supernatant of the cells was recovered and concentrated 10-fold using centricon-10 (trade name, AMICON). Samples were subjected to SDS-polyacrylamide-gel electrophoresis. The gel was dried and $^{35}$S-labeled proteins were detected with BAS 2000 (Fuji Film).

A band was detected at 60–70 kDa in the supernatant of pNotS-mA55-transfected 293T cells. This band was not detected in the supernatant of pNotS-transfected 293T cells. This result confirmed that recombinant mouse A55 protein was expressed and secreted into the medium. Molecular weight (60–70 kDa) of recombinant mouse A55 protein was greater than predicted (48 kDa) from its amino acid sequences. As this protein had two potential N-linked glycosylation sites and many Ser and Thr residues in which O-linked glycosyl chain could be added, it was suggested that the mouse A55 protein was a glycoprotein.

EXAMPLE 7

Measurement of Inhibition on Proliferation of Rat Vascular Smooth Muscle Cells by Mouse A55 Protein Vascular smooth muscle cells were isolated from rat aorta ranging from heart to diaphragm and cultured primarily by the methods described in Shin Seikagaku Jikken Kouza 10 (The Japanese Biochemical Society). These cells were co-incubated with 1, 3 or 10 ng/ml of human recombinant PDGF-BB (Genzyme) and 10% (v/v) of the mock or mA55 supernatant prepared according to the method described in example 7. BrdU incorporation was measured using a Cell Proliferation ELISA, BrdU calorimetric kit (Boehringer-Mannheim).

When BrdU (bromodeoxyuracil) is added to cultured cells, it is incorporated into genomic DNA via DNA replication accompanying cellular proliferation. Cells which were grown in the presence of BrdU are immobilized and then the amount of incorporated BrdU is measured by ELISA using a labeled anti-BrdU antibody. The measured relative amount of BrdU indicates the degree of DNA replication so that the BrdU assay it can be used as an index of cell proliferation.

The supernatant from 293T cells transfected with pNotS-mA55 significantly inhibited BrdU incorporation of rat primary vascular smooth muscle cells, while the supernatant from 293T cells transfected with only pNotS show no effect as shown in FIG. 1.

Moreover, the supernatant from 293T cells transfected with pNotS-mA55 also inhibited BrdU incorporation even when rat vascular smooth muscle cells were stimulated with 1, 3 or 10 ng/ml of PDGF and increased BrdU incorporation in a dose-dependent manner, whereas the supernatant from 293T cells transfected with only pNotS had no effect when compared with no supernatant addition (see FIG. 1).

These data revealed that the recombinant mouse A55 protein had growth inhibitory activity on vascular smooth muscle cells.

EXPERIMENT 8

Preparation of Anti-mouse A55 Polyclonal Antibody

Three kinds of peptide fragments of mouse A55 were synthesized by solid phase method:

| | |
|---|---|
| RTNPVYRGPYSNPYSTSYSG (71–90) | (48–67 of SEQ ID NO: 3) |
| GAYYIFQIKSGNEGREFYMR (376–395) | (353–372 of SEQ ID NO: 3) |
| MTRPIKGPRDIQLDLEMITVN (406–426) | (383–403 of SEQ ID NO: 3). |

Rabbits were immunized using these peptides as immunogens and serum was prepared after measurement of the activity. Each anti-mouse A55 antibody was purified by affinity column using the immunogens as immobilized peptides.

The supernatant prepared by the same method described in example 6 was subjected to SDS-PAGE, and the separated proteins were transferred to Immobilon-P (PVDF membrane, trade name, Millipore) from the acrylamide gel. After blocking the membranes, they were incubated with the anti-mouse A55 polyclonal antibody as the first antibody and by developing using ECL kit (Amersham), and the recombinant mouse A55 protein was detected.

A 60 kDa band was detected in the supernatant from mA55-transfected Cos1 cells as well as in the $^{35}$S-labeling experiment described in example 7. No bands were detected in the supernatant from mock-transfected Cos1 cells. These results confirmed that the obtained polyclonal. antibodies specifically recognized the mouse A55 protein.

What is claimed is:

1. An isolated polypeptide comprising the amino acid sequence shown in SEQ ID NO. 3, 8, 9, or a homologue thereof having at least 95% sequence identity over the full length of the amino acid sequence, wherein said polypeptide suppresses smooth muscle cell proliferation.

2. The isolated polypeptide according to claim 1 comprising the amino acid sequence shown in SEQ ID NO. 3, 8 or 9.

3. A pharmaceutical composition comprising the polypeptide according to claim 1 or 2, in association with a pharmaceutically acceptable diluent or carrier, or both.

4. An isolated cDNA comprising a nucleotide sequence encoding a polypeptide comprising the amino acid sequence shown in SEQ ID NO. 3, 8, 9, or a homologue thereof having at least 95% sequence identity over the full-length of the amino acid sequence, wherein said polypeptide suppresses smooth muscle cell proliferation.

5. The isolated cDNA according to claim 4, wherein the cDNA comprises a nucleotide sequence encoding a polypeptide comprising the amino acid sequence shown in SEQ ID NO: 3, 8 or 9, and wherein said polypeptide suppresses smooth muscle cell proliferation.

6. An isolated cDNA comprising the nucleotide sequence shown in SEQ ID NO: 1, 6, 10, or a homologue thereof having at least 95% sequence identity over the full length of the nucleotide sequence, wherein said nucleotide sequence encodes a polypeptide that suppresses smooth muscle cell proliferation.

7. The isolated cDNA according to claim 4 comprising the nucleotide sequence shown in SEQ ID NO. 1, 6 or 10.

8. The isolated cDNA according to claim 4 comprising the nucleotide sequence shown in SEQ ID NO. 2 or 7.

9. A replication or expression vector comprising, the cDNA according to any one of claims 4, 7, or 8.

10. A host cell transformed with the replication or expression vector according to claim 9.

11. A method for producing a polypeptide of SEQ ID NO: 3, 8 or 9, or a homologue thereof having at least 95% sequence identity over the full length of the amino acid sequence, wherein said polypeptide suppresses smooth muscle cell proliferation, comprising culturing a host cell of claim 10 under a condition effective to express the polypeptide, and recovering the polypeptide so expressed.

12. A method for screening for an antagonist or antagonist of a polypeptide according to claim 1 or 2, said method comprising preparing a first and second culture of a cell line, culturing said first cell line in the presence of one or more of said polypeptides, culturing said second cell line in the presence of one or more of said polypeptides and a test compound, and comparing the proliferation of the two cultures, thereby screening for an antagonist or antagonist of a polypeptide according to claim 1 or 2.

* * * * *

SEQUENCE LISTING

<160> NUMBER OF SEQ ID NOS: 12

<210> SEQ ID NO 1
<211> LENGTH: 1344
<212> TYPE: DNA
<213> ORGANISM: Mus musculus

<400> SEQUENCE: 1

```
atgccaggat taaaaggat  actcactgtt accatcttgg cactctggct tccacatcct     60
gggaatgcac agcagcagtg cacaaacggc tttgacctgg accgccagtc aggacagtgt    120
ctagatattg atgaatgccg gaccatccct gaggcttgtc gtggggacat gatgtgtgtc    180
aaccagaatg gcgggtattt gtgcatccct cgaaccaacc cagtgtatcg agggccttac    240
tcaaatccct actctacatc ctactcaggc ccatacccag cagcggcccc accagtacca    300
gcttccaact accccacgat tcaaggcct  cttgtctgcc gctttgggta tcagatggat    360
gaaggcaacc agtgtgtgga tgtggacgag tgtgcaacag actcacacca gtgcaaccct    420
acccagatct gtatcaacac tgaaggaggt tacacctgct cctgcaccga tgggtactgg    480
cttctggaag ggcagtgcct agatattgat gaatgtcgct atggttactg ccagcagctc    540
tgtgcaaatg ttccaggatc ctattcctgt acatgcaacc ctggtttcac cctcaacgac    600
gatggaaggt cttgccaaga tgtgaacgag tgcgaaactg agaatccctg tgttcagacc    660
tgtgtcaaca cctatggctc tttcatctgc cgctgtgacc aggatatgga acttgaggaa    720
gatggcattc actgcagtga tatggacgag tgcagcttct ccgagttcct ctgtcaacac    780
gagtgtgtga accagccggg ctcatacttc tgctcgtgcc ctccaggcta cgtcctgttg    840
gatgataacc gaagctgcca ggatatcaat gaatgtgagc accgaaacca cacgtgtacc    900
tcactgcaga cttgctacaa tctacaaggg ggcttcaaat gtattgatcc catcagctgt    960
gaggagcctt atctgctgat tggtgaaaac cgctgtatgt gtcctgctga gcacaccagc   1020
tgcagagacc agccattcac catcctgtat cgggacatgg atgtggtgtc aggacgctcc   1080
gttcctgctg acatcttcca gatgcaagca acaacccgat accctggtgc ctattacatt   1140
ttccagatca aatctggcaa cgagggtcga gagttctata tgcggcaaac agggcctatc   1200
agtgccaccc tggtgatgac acgccccatc aaagggcctc gggacatcca gctggacttg   1260
gagatgatca ctgtcaacac tgtcatcaac ttcagaggca gctccgtgat ccgactgcgg   1320
atatatgtgt cgcagtatcc gttc                                         1344
```

<210> SEQ ID NO 2
<211> LENGTH: 2233
<212> TYPE: DNA
<213> ORGANISM: Mus musculus
<220> FEATURE:
<221> NAME/KEY: misc_feature
<223> OTHER INFORMATION: Clone mouse A55 derived from Day 13 mouse
      embryonic heart
<221> NAME/KEY: misc_feature
<223> OTHER INFORMATION: "n" may be either a, c, g or t
<221> NAME/KEY: CDS
<222> LOCATION: (75)..(1418)
<221> NAME/KEY: sig_peptide
<222> LOCATION: (75)..(143)
<221> NAME/KEY: mat_peptide
<222> LOCATION: (144)..()

<400> SEQUENCE: 2

```
aattcggcac gagccccagt cccaccgcag agcctgcctt cctcgcgtcg cttctcctcc     60
```

-continued

| | | |
|---|---|---|
| cgcgcatctt ggat atg cca gga tta aaa agg ata ctc act gtt acc atc<br>             Met Pro Gly Leu Lys Arg Ile Leu Thr Val Thr Ile<br>                    -20                               -15 | | 110 |
| ttg gca ctc tgg ctt cca cat cct ggg aat gca cag cag cag tgc aca<br>Leu Ala Leu Trp Leu Pro His Pro Gly Asn Ala Gln Gln Gln Cys Thr<br>    -10                  -5                 -1  1               5 | | 158 |
| aac ggc ttt gac ctg gac cgc cag tca gga cag tgt cta gat att gat<br>Asn Gly Phe Asp Leu Asp Arg Gln Ser Gly Gln Cys Leu Asp Ile Asp<br>             10                    15                  20 | | 206 |
| gaa tgc cgg acc atc cct gag gct tgt cgt ggg gac atg atg tgt gtc<br>Glu Cys Arg Thr Ile Pro Glu Ala Cys Arg Gly Asp Met Met Cys Val<br>          25                  30                  35 | | 254 |
| aac cag aat ggc ggg tat ttg tgc atc cct cga acc aac cca gtg tat<br>Asn Gln Asn Gly Gly Tyr Leu Cys Ile Pro Arg Thr Asn Pro Val Tyr<br>          40                  45                  50 | | 302 |
| cga ggg cct tac tca aat ccc tac tct aca tcc tac tca ggc cca tac<br>Arg Gly Pro Tyr Ser Asn Pro Tyr Ser Thr Ser Tyr Ser Gly Pro Tyr<br>          55                  60                  65 | | 350 |
| cca gca gcg gcc cca cca gta cca gct tcc aac tac ccc acg att tca<br>Pro Ala Ala Ala Pro Pro Val Pro Ala Ser Asn Tyr Pro Thr Ile Ser<br>70                  75                  80                  85 | | 398 |
| agg cct ctt gtc tgc cgc ttt ggg tat cag atg gat gaa ggc aac cag<br>Arg Pro Leu Val Cys Arg Phe Gly Tyr Gln Met Asp Glu Gly Asn Gln<br>             90                  95                100 | | 446 |
| tgt gtg gat gtg gac gag tgt gca aca gac tca cac cag tgc aac cct<br>Cys Val Asp Val Asp Glu Cys Ala Thr Asp Ser His Gln Cys Asn Pro<br>             105                  110                115 | | 494 |
| acc cag atc tgt atc aac act gaa gga ggt tac acc tgc tcc tgc acc<br>Thr Gln Ile Cys Ile Asn Thr Glu Gly Gly Tyr Thr Cys Ser Cys Thr<br>          120                  125                130 | | 542 |
| gat ggg tac tgg ctt ctg gaa ggg cag tgc cta gat att gat gaa tgt<br>Asp Gly Tyr Trp Leu Leu Glu Gly Gln Cys Leu Asp Ile Asp Glu Cys<br>          135                  140                145 | | 590 |
| cgc tat ggt tac tgc cag cag ctc tgt gca aat gtt cca gga tcc tat<br>Arg Tyr Gly Tyr Cys Gln Gln Leu Cys Ala Asn Val Pro Gly Ser Tyr<br>150                 155                  160                 165 | | 638 |
| tcc tgt aca tgc aac cct ggt ttc acc ctc aac gac gat gga agg tct<br>Ser Cys Thr Cys Asn Pro Gly Phe Thr Leu Asn Asp Asp Gly Arg Ser<br>               170                  175                180 | | 686 |
| tgc caa gat gtg aac gag tgc gaa act gag aat ccc tgt gtt cag acc<br>Cys Gln Asp Val Asn Glu Cys Glu Thr Glu Asn Pro Cys Val Gln Thr<br>          185                  190                195 | | 734 |
| tgt gtc aac acc tat ggc tct ttc atc tgc cgc tgt gac cca gga tat<br>Cys Val Asn Thr Tyr Gly Ser Phe Ile Cys Arg Cys Asp Pro Gly Tyr<br>          200                  205                210 | | 782 |
| gaa ctt gag gaa gat ggc att cac tgc agt gat atg gac gag tgc agc<br>Glu Leu Glu Glu Asp Gly Ile His Cys Ser Asp Met Asp Glu Cys Ser<br>          215                  220                225 | | 830 |
| ttc tcc gag ttc ctc tgt caa cac gag tgt gtg aac cag ccg ggc tca<br>Phe Ser Glu Phe Leu Cys Gln His Glu Cys Val Asn Gln Pro Gly Ser<br>230                 235                  240                 245 | | 878 |
| tac ttc tgc tcg tgc cct cca ggc tac gtc ctg ttg gat gat aac cga<br>Tyr Phe Cys Ser Cys Pro Pro Gly Tyr Val Leu Leu Asp Asp Asn Arg<br>               250                  255                260 | | 926 |
| agc tgc cag gat atc aat gaa tgt gag cac cga aac cac acg tgt acc<br>Ser Cys Gln Asp Ile Asn Glu Cys Glu His Arg Asn His Thr Cys Thr<br>             265                  270                275 | | 974 |
| tca ctg cag act tgc tac aat cta caa ggg ggc ttc aaa tgt att gat<br>Ser Leu Gln Thr Cys Tyr Asn Leu Gln Gly Gly Phe Lys Cys Ile Asp | | 1022 |

```
ccc atc agc tgt gag gag cct tat ctg ctg att ggt gaa aac cgc tgt    1070
Pro Ile Ser Cys Glu Glu Pro Tyr Leu Leu Ile Gly Glu Asn Arg Cys
    295             300             305 atg tgt cct gct gag cac acc agc tgc aga gac cag cca ttc acc atc    1118
Met Cys Pro Ala Glu His Thr Ser Cys Arg Asp Gln Pro Phe Thr Ile
310             315             320             325 ctg tat cgg gac atg gat gtg gtg tca gga cgc tcc gtt cct gct gac    1166
Leu Tyr Arg Asp Met Asp Val Val Ser Gly Arg Ser Val Pro Ala Asp
            330             335             340 atc ttc cag atg caa gca aca acc cga tac cct ggt gcc tat tac att    1214
Ile Phe Gln Met Gln Ala Thr Thr Arg Tyr Pro Gly Ala Tyr Tyr Ile
        345             350             355 ttc cag atc aaa tct ggc aac gag ggt cga gag ttc tat atg cgg caa    1262
Phe Gln Ile Lys Ser Gly Asn Glu Gly Arg Glu Phe Tyr Met Arg Gln
    360             365             370 aca ggg cct atc agt gcc acc ctg gtg atg aca cgc ccc atc aaa ggg    1310
Thr Gly Pro Ile Ser Ala Thr Leu Val Met Thr Arg Pro Ile Lys Gly
375             380             385 cct cgg gac atc cag ctg gac ttg gag atg atc act gtc aac act gtc    1358
Pro Arg Asp Ile Gln Leu Asp Leu Glu Met Ile Thr Val Asn Thr Val
390             395             400             405 atc aac ttc aga ggc agc tcc gtg atc cga ctg cgg ata tat gtg tcg    1406
Ile Asn Phe Arg Gly Ser Ser Val Ile Arg Leu Arg Ile Tyr Val Ser
            410             415             420 cag tat ccg ttc tgagcctctg gctaaggcct ctgacactgc ctttcaccag        1458
Gln Tyr Pro Phe
        425 caccgaggga cgggaggaga aaggaaacca gcaagaatga gagcgagaca gacattgcac    1518 cttttcctgct gaatatctcc tggggcatc agcctagcat cttgacccat atctgtacta   1578 ttgcagatgg tcactctgaa ggacaccctg ccctcagttc ctatgatgca gttatccaaa   1638 agtgttcatc ttagcccctg atatgaggtt gccagtgact cttcaaagcc ttccatttat   1698 ttccatcgtt ttataaaaaa gaaaatagat tagatttgct ggggtatgag tcctcgaagg   1758 ttcaaaagac tgagtggctt gctctcacct cttcctctcc ttcctccatc tcttgctgca   1818 ttgctgcttt gcaaaagtcc tcatgggctc gtgggaaatg ctgggaatag ctagtttgct   1878 tcttgcatgt tctgagaagg ctatgggaac acaccacagc aggatcgaag gttttttatag  1938 agtctatttt aaaatcacat ctggtatttt cagcataaaa gaaatttag ttgtctttaa    1998 aatttgtatg agtgtttaac cttttcttat tcatttgag gcttcttaaa gtggtagaat    2058 tccttccaaa ggcctcagat acatgttatg ttcagtcttt ccaacctcat cctttcctgc   2118 atcttagccc agttttacg aagacccctt aatcatgctt tnttaagagt ttttacccaa    2178 ctgcgttgga agacagaggt atccagactg attaaataat tgaagaaaaa aaaaa        2233
```

<210> SEQ ID NO 3
<211> LENGTH: 448
<212> TYPE: PRT
<213> ORGANISM: Mus musculus
<220> FEATURE:
<221> NAME/KEY: misc_feature
<223> OTHER INFORMATION: Clone mouse A55 derived from Day 13 mouse
      embryonic heart

<400> SEQUENCE: 3

Met Pro Gly Leu Lys Arg Ile Leu Thr Val Thr Ile Leu Ala Leu Trp
        -20             -15             -10

```
Leu Pro His Pro Gly Asn Ala Gln Gln Cys Thr Asn Gly Phe Asp
        -5              -1   1              5
Leu Asp Arg Gln Ser Gly Gln Cys Leu Asp Ile Asp Glu Cys Arg Thr
10              15              20              25
Ile Pro Glu Ala Cys Arg Gly Asp Met Met Cys Val Asn Gln Asn Gly
                30              35              40
Gly Tyr Leu Cys Ile Pro Arg Thr Asn Pro Val Tyr Arg Gly Pro Tyr
            45              50              55
Ser Asn Pro Tyr Ser Thr Ser Tyr Ser Gly Pro Tyr Pro Ala Ala Ala
        60              65              70
Pro Pro Val Pro Ala Ser Asn Tyr Pro Thr Ile Ser Arg Pro Leu Val
75              80              85
Cys Arg Phe Gly Tyr Gln Met Asp Glu Gly Asn Gln Cys Val Asp Val
90              95              100             105
Asp Glu Cys Ala Thr Asp Ser His Gln Cys Asn Pro Thr Gln Ile Cys
                110             115             120
Ile Asn Thr Glu Gly Gly Tyr Thr Cys Ser Cys Thr Asp Gly Tyr Trp
            125             130             135
Leu Leu Glu Gly Gln Cys Leu Asp Ile Asp Glu Cys Arg Tyr Gly Tyr
        140             145             150
Cys Gln Gln Leu Cys Ala Asn Val Pro Gly Ser Tyr Ser Cys Thr Cys
155             160             165
Asn Pro Gly Phe Thr Leu Asn Asp Asp Gly Arg Ser Cys Gln Asp Val
170             175             180             185
Asn Glu Cys Glu Thr Glu Asn Pro Cys Val Gln Thr Cys Val Asn Thr
                190             195             200
Tyr Gly Ser Phe Ile Cys Arg Cys Asp Pro Gly Tyr Glu Leu Glu Glu
            205             210             215
Asp Gly Ile His Cys Ser Asp Met Asp Glu Cys Ser Phe Ser Glu Phe
        220             225             230
Leu Cys Gln His Glu Cys Val Asn Gln Pro Gly Ser Tyr Phe Cys Ser
235             240             245
Cys Pro Pro Gly Tyr Val Leu Leu Asp Asp Asn Arg Ser Cys Gln Asp
250             255             260             265
Ile Asn Glu Cys Glu His Arg Asn His Thr Cys Thr Ser Leu Gln Thr
                270             275             280
Cys Tyr Asn Leu Gln Gly Gly Phe Lys Cys Ile Asp Pro Ile Ser Cys
            285             290             295
Glu Glu Pro Tyr Leu Leu Ile Gly Glu Asn Arg Cys Met Cys Pro Ala
        300             305             310
Glu His Thr Ser Cys Arg Asp Gln Pro Phe Thr Ile Leu Tyr Arg Asp
315             320             325
Met Asp Val Val Ser Gly Arg Ser Val Pro Ala Asp Ile Phe Gln Met
330             335             340             345
Gln Ala Thr Thr Arg Tyr Pro Gly Ala Tyr Tyr Ile Phe Gln Ile Lys
                350             355             360
Ser Gly Asn Glu Gly Arg Glu Phe Tyr Met Arg Gln Thr Gly Pro Ile
            365             370             375
Ser Ala Thr Leu Val Met Thr Arg Pro Ile Lys Gly Pro Arg Asp Ile
        380             385             390
Gln Leu Asp Leu Glu Met Ile Thr Val Asn Thr Val Ile Asn Phe Arg
395             400             405
Gly Ser Ser Val Ile Arg Leu Arg Ile Tyr Val Ser Gln Tyr Pro Phe
```

<210> SEQ ID NO 4
<211> LENGTH: 423
<212> TYPE: PRT
<213> ORGANISM: Mus musculus

<400> SEQUENCE: 4

```
Gln Cys Thr Asn Gly Phe Asp Leu Asp Arg Gln Ser Gly Gln Cys Leu
  1               5                  10                  15

Asp Ile Asp Glu Cys Arg Thr Ile Pro Glu Ala Cys Arg Gly Asp Met
             20                  25                  30

Met Cys Val Asn Gln Asn Gly Gly Tyr Leu Cys Ile Pro Arg Thr Asn
         35                  40                  45

Pro Val Tyr Arg Gly Pro Tyr Ser Asn Pro Tyr Ser Thr Ser Tyr Ser
     50                  55                  60

Gly Pro Tyr Pro Ala Ala Ala Pro Pro Val Pro Ala Ser Asn Tyr Pro
 65                  70                  75                  80

Thr Ile Ser Arg Pro Leu Val Cys Arg Phe Gly Tyr Gln Met Asp Glu
             85                  90                  95

Gly Asn Gln Cys Val Asp Val Asp Glu Cys Ala Thr Asp Ser His Gln
            100                 105                 110

Cys Asn Pro Thr Gln Ile Cys Ile Asn Thr Glu Gly Gly Tyr Thr Cys
            115                 120                 125

Ser Cys Thr Asp Gly Tyr Trp Leu Leu Glu Gly Gln Cys Leu Asp Ile
        130                 135                 140

Asp Glu Cys Arg Tyr Gly Tyr Cys Gln Gln Leu Cys Ala Asn Val Pro
145                 150                 155                 160

Gly Ser Tyr Ser Cys Thr Cys Asn Pro Gly Phe Thr Leu Asn Asp Asp
                165                 170                 175

Gly Arg Ser Cys Gln Asp Val Asn Glu Cys Glu Thr Glu Asn Pro Cys
            180                 185                 190

Val Gln Thr Cys Val Asn Thr Tyr Gly Ser Phe Ile Cys Arg Cys Asp
            195                 200                 205

Pro Gly Tyr Glu Leu Glu Glu Asp Gly Ile His Cys Ser Asp Met Asp
        210                 215                 220

Glu Cys Ser Phe Ser Glu Phe Leu Cys Gln His Glu Cys Val Asn Gln
225                 230                 235                 240

Pro Gly Ser Tyr Phe Cys Ser Cys Pro Pro Gly Tyr Val Leu Leu Asp
                245                 250                 255

Asp Asn Arg Ser Cys Gln Asp Ile Asn Glu Cys Glu His Arg Asn His
            260                 265                 270

Thr Cys Thr Ser Leu Gln Thr Cys Tyr Asn Leu Gln Gly Gly Phe Lys
        275                 280                 285

Cys Ile Asp Pro Ile Ser Cys Glu Glu Pro Tyr Leu Leu Ile Gly Glu
            290                 295                 300

Asn Arg Cys Met Cys Pro Ala Glu His Thr Ser Cys Arg Asp Gln Pro
305                 310                 315                 320

Phe Thr Ile Leu Tyr Arg Asp Met Asp Val Val Ser Gly Arg Ser Val
                325                 330                 335

Pro Ala Asp Ile Phe Gln Met Gln Ala Thr Thr Arg Tyr Pro Gly Ala
            340                 345                 350

Tyr Tyr Ile Phe Gln Ile Lys Ser Gly Asn Glu Gly Arg Glu Phe Tyr
        355                 360                 365
```

```
Met Arg Gln Thr Gly Pro Ile Ser Ala Thr Leu Val Met Thr Arg Pro
        370                 375                 380

Ile Lys Gly Pro Arg Asp Ile Gln Leu Asp Leu Glu Met Ile Thr Val
385                 390                 395                 400

Asn Thr Val Ile Asn Phe Arg Gly Ser Ser Val Ile Arg Leu Arg Ile
                405                 410                 415

Tyr Val Ser Gln Tyr Pro Phe
            420

<210> SEQ ID NO 5
<211> LENGTH: 1269
<212> TYPE: DNA
<213> ORGANISM: Mus musculus

<400> SEQUENCE: 5
cagtgcacaa acggctttga cctggaccgc cagtcaggac agtgtctaga tattgatgaa      60
tgccggacca tccctgaggc ttgtcgtggg gacatgatgt gtgtcaacca gaatggcggg     120
tatttgtgca tccctcgaac caacccagtg tatcgagggc ttactcaaa tccctactct      180 acatcctact caggcccata cccagcagcg gccccaccag taccagcttc caactacccc     240
acgatttcaa ggcctcttgt ctgccgcttt gggtatcaga tggatgaagg caaccagtgt     300
gtggatgtgg acgagtgtgc aacagactca caccagtgca accctaccca gatctgtatc     360
aacactgaag gaggttacac ctgctcctgc accgatgggt actggcttct ggaagggcag     420
tgcctagata ttgatgaatg tcgctatggt tactgccagc agctctgtgc aaatgttcca     480
ggatcctatt cctgtacatg caaccctggt ttcaccctca cgacgatgg aaggtcttgc      540 caagatgtga cgagtgcga aactgagaat ccctgtgttc agacctgtgt caacaccctat     600 ggctctttca tctgccgctg tgacccagga tatgaacttg aggaagatgg cattcactgc     660
agtgatatgg acgagtgcag cttctccgag ttcctctgtc aacacgagtg tgtgaaccag     720
ccgggctcat acttctgctc gtgccctcca ggctacgtcc tgttggatga taaccgaagc     780
tgccaggata tcaatgaatg tgagcaccga accacacgt gtacctcact gcagacttgc     840
tacaatctac aagggggctt caaatgtatt gatcccatca gctgtgagga gccttatctg     900
ctgattggtg aaaaccgctg tatgtgtcct gctgagcaca ccagctgcag agaccagcca     960
ttcaccatcc tgtatcggga catggatgtg gtgtcaggac gctccgttcc tgctgacatc    1020
ttccagatgc aagcaacaac ccgatacct ggtgcctatt acattttcca gatcaaatct     1080
ggcaacgagg gtcgagagtt ctatatgcgg caaaacgggc ctatcagtgc caccctggtg    1140
atgacacgcc ccatcaaagg gcctcgggac atccagctgg acttggagat gatcactgtc    1200
aacactgtca tcaacttcag aggcagctcc gtgatccgac tgcggatata tgtgtcgcag    1260
tatccgttc                                                           1269

<210> SEQ ID NO 6
<211> LENGTH: 1383
<212> TYPE: DNA
<213> ORGANISM: Mus musculus

<400> SEQUENCE: 6
atgggaccta gaagtttcga gccaatgcac agtggactct gcagacagag acgcatgata      60
ctcactgtta ccatcttggc actctggctt ccacatcctg gaatgcaca gcagcagtgc     120 acaaacggct ttgacctgga ccgccagtca ggacagtgtc tagatattga tgaatgccgg     180
accatccctg aggcttgtcg tggggacatg atgtgtgtca accagaatgg cgggtatttg     240
```

```
tgcatccctc gaaccaaccc agtgtatcga gggccttact caaatccctact ctctacatcc      300 tactcaggcc catacccagc agcggcccca ccagtaccag cttccaacta ccccacgatt      360
tcaaggcctc ttgtctgccg ctttgggtat cagatggatg aaggcaacca gtgtgtggat      420
gtggacgagt gtgcaacaga ctcacaccag tgcaacccta cccagatctg tatcaacact      480
gaaggaggtt acacctgctc ctgcaccgat gggtactggc ttctggaagg gcagtgccta      540
gatattgatg aatgtcgcta tggttactgc cagcagctct gtgcaaatgt tccaggatcc      600
tattcctgta catgcaaccc tggtttcacc ctcaacgacg atggaaggtc ttgccaagat      660
gtgaacgagt gcgaaactga aatccctgt gttcagacct gtgtcaacac ctatggctct      720
ttcatctgcc gctgtgaccc aggatatgaa cttgaggaag atggcattca ctgcagtgat      780
atggacgagt gcagcttctc cgagttcctc tgtcaacacg agtgtgtgaa ccagccgggc      840
tcatacttct gctcgtgccc tccaggctac gtcctgttgg atgataaccg aagctgccag      900
gatatcaatg aatgtgagca ccgaaaccac acgtgtacct cactgcagac ttgctacaat      960
ctacaagggg gcttcaaatg tattgatccc atcagctgtg aggagcctta tctgctgatt     1020
ggtgaaaacc gctgtatgtg tcctgctgag cacaccagct gcagagacca gccattcacc     1080
atcctgtatc gggacatgga tgtggtgtca ggacgctccg ttcctgctga catcttccag     1140
atgcaagcaa caacccgata ccctggtgcc tattacattt tccagatcaa atctggcaac     1200
gagggtcgag agttctatat gcggcaaaca gggcctatca gtgccaccct ggtgatgaca     1260
cgccccatca aagggcctcg ggacatccag ctggacttgg agatgatcac tgtcaacact     1320
gtcatcaact tcagaggcag ctccgtgatc cgactgcgga tatatgtgtc gcagtatccg     1380
ttc                                                                   1383

<210> SEQ ID NO 7
<211> LENGTH: 2429
<212> TYPE: DNA
<213> ORGANISM: Mus musculus
<220> FEATURE:
<221> NAME/KEY: misc_feature
<223> OTHER INFORMATION: Clone mouse A55b derived from Day 13 mouse
      embryonic heart
<221> NAME/KEY: misc_feature
<223> OTHER INFORMATION: "n" can be a, c, g or t
<221> NAME/KEY: sig_peptide
<222> LOCATION: (232)..(339)
<221> NAME/KEY: mat_peptide
<222> LOCATION: (340)..()
<221> NAME/KEY: CDS
<222> LOCATION: (232)..(1614)

<400> SEQUENCE: 7
cagcatctcg agagaggcag cagacaacct ctctaggtca tttctctttc tttttggaaa       60
gggcagcaac gttgtgcgca gtttataaaa tatcacacta catgtttttt aaatttggga      120
gactgctgac tacggcacca gcaattgctt tgctgcgacg gctgtgagac aagcagaagt      180
ctccgaacac ttctgtctgc gtttgctcta tgtgtgtgat ttacagaggg a atg gga      237
                                                        Met Gly
                                                        -35 cct aga agt ttc gag cca atg cac agt gga ctc tgc aga cag aga cgc      285
Pro Arg Ser Phe Glu Pro Met His Ser Gly Leu Cys Arg Gln Arg Arg
        -30                 -25                 -20 atg ata ctc act gtt acc atc ttg gca ctc tgg ctt cca cat cct ggg      333
Met Ile Leu Thr Val Thr Ile Leu Ala Leu Trp Leu Pro His Pro Gly
    -15                 -10                  -5
```

-continued

| | | |
|---|---|---|
| aat gca cag cag cag tgc aca aac ggc ttt gac ctg gac cgc cag tca<br>Asn Ala Gln Gln Gln Cys Thr Asn Gly Phe Asp Leu Asp Arg Gln Ser<br>    -1  1               5                    10 | | 381 |
| gga cag tgt cta gat att gat gaa tgc cgg acc atc cct gag gct tgt<br>Gly Gln Cys Leu Asp Ile Asp Glu Cys Arg Thr Ile Pro Glu Ala Cys<br>15               20                25               30 | | 429 |
| cgt ggg gac atg atg tgt gtc aac cag aat ggc ggg tat ttg tgc atc<br>Arg Gly Asp Met Met Cys Val Asn Gln Asn Gly Gly Tyr Leu Cys Ile<br>               35                40             45 | | 477 |
| cct cga acc aac cca gtg tat cga ggg cct tac tca aat ccc tac tct<br>Pro Arg Thr Asn Pro Val Tyr Arg Gly Pro Tyr Ser Asn Pro Tyr Ser<br>      50                    55                60 | | 525 |
| aca tcc tac tca ggc cca tac cca gca gcg gcc cca cca gta cca gct<br>Thr Ser Tyr Ser Gly Pro Tyr Pro Ala Ala Ala Pro Pro Val Pro Ala<br>     65                   70                75 | | 573 |
| tcc aac tac ccc acg att tca agg cct ctt gtc tgc cgc ttt ggg tat<br>Ser Asn Tyr Pro Thr Ile Ser Arg Pro Leu Val Cys Arg Phe Gly Tyr<br>    80                   85                90 | | 621 |
| cag atg gat gaa ggc aac cag tgt gtg gat gtg gac gag tgt gca aca<br>Gln Met Asp Glu Gly Asn Gln Cys Val Asp Val Asp Glu Cys Ala Thr<br>95                 100              105            110 | | 669 |
| gac tca cac cag tgc aac cct acc cag atc tgt atc aac act gaa gga<br>Asp Ser His Gln Cys Asn Pro Thr Gln Ile Cys Ile Asn Thr Glu Gly<br>         115              120            125 | | 717 |
| ggt tac acc tgc tcc tgc acc gat ggg tac tgg ctt ctg gaa ggg cag<br>Gly Tyr Thr Cys Ser Cys Thr Asp Gly Tyr Trp Leu Leu Glu Gly Gln<br>        130               135             140 | | 765 |
| tgc cta gat att gat gaa tgt cgc tat ggt tac tgc cag cag ctc tgt<br>Cys Leu Asp Ile Asp Glu Cys Arg Tyr Gly Tyr Cys Gln Gln Leu Cys<br>         145              150            155 | | 813 |
| gca aat gtt cca gga tcc tat tcc tgt aca tgc aac cct ggt ttc acc<br>Ala Asn Val Pro Gly Ser Tyr Ser Cys Thr Cys Asn Pro Gly Phe Thr<br>160                 165               170 | | 861 |
| ctc aac gac gat gga agg tct tgc caa gat gtg aac gag tgc gaa act<br>Leu Asn Asp Asp Gly Arg Ser Cys Gln Asp Val Asn Glu Cys Glu Thr<br>175                 180              185            190 | | 909 |
| gag aat ccc tgt gtt cag acc tgt gtc aac acc tat ggc tct ttc atc<br>Glu Asn Pro Cys Val Gln Thr Cys Val Asn Thr Tyr Gly Ser Phe Ile<br>         195              200            205 | | 957 |
| tgc cgc tgt gac cca gga tat gaa ctt gag gaa gat ggc att cac tgc<br>Cys Arg Cys Asp Pro Gly Tyr Glu Leu Glu Glu Asp Gly Ile His Cys<br>         210              215            220 | | 1005 |
| agt gat atg gac gag tgc agc ttc tcc gag ttc ctc tgt caa cac gag<br>Ser Asp Met Asp Glu Cys Ser Phe Ser Glu Phe Leu Cys Gln His Glu<br>         225              230            235 | | 1053 |
| tgt gtg aac cag ccg ggc tca tac ttc tgc tcg tgc cct cca ggc tac<br>Cys Val Asn Gln Pro Gly Ser Tyr Phe Cys Ser Cys Pro Pro Gly Tyr<br>240                 245               250 | | 1101 |
| gtc ctg ttg gat gat aac cga agc tgc cag gat atc aat gaa tgt gag<br>Val Leu Leu Asp Asp Asn Arg Ser Cys Gln Asp Ile Asn Glu Cys Glu<br>255                 260              265            270 | | 1149 |
| cac cga aac cac acg tgt acc tca ctg cag act tgc tac aat cta caa<br>His Arg Asn His Thr Cys Thr Ser Leu Gln Thr Cys Tyr Asn Leu Gln<br>         275              280            285 | | 1197 |
| ggg ggc ttc aaa tgt att gat ccc atc agc tgt gag gag cct tat ctg<br>Gly Gly Phe Lys Cys Ile Asp Pro Ile Ser Cys Glu Glu Pro Tyr Leu<br>         290              295            300 | | 1245 |
| ctg att ggt gaa aac cgc tgt atg tgt cct gct gag cac acc agc tgc<br>Leu Ile Gly Glu Asn Arg Cys Met Cys Pro Ala Glu His Thr Ser Cys<br>         305              310            315 | | 1293 |

-continued

```
aga gac cag cca ttc acc atc ctg tat cgg gac atg gat gtg gtg tca     1341
Arg Asp Gln Pro Phe Thr Ile Leu Tyr Arg Asp Met Asp Val Val Ser
    320                 325                 330 gga cgc tcc gtt cct gct gac atc ttc cag atg caa gca aca acc cga     1389
Gly Arg Ser Val Pro Ala Asp Ile Phe Gln Met Gln Ala Thr Thr Arg
335                 340                 345                 350 tac cct ggt gcc tat tac att ttc cag atc aaa tct ggc aac gag ggt     1437
Tyr Pro Gly Ala Tyr Tyr Ile Phe Gln Ile Lys Ser Gly Asn Glu Gly
                355                 360                 365 cga gag ttc tat atg cgg caa aca ggg cct atc agt gcc acc ctg gtg     1485
Arg Glu Phe Tyr Met Arg Gln Thr Gly Pro Ile Ser Ala Thr Leu Val
            370                 375                 380 atg aca cgc ccc atc aaa ggg cct cgg gac atc cag ctg gac ttg gag     1533
Met Thr Arg Pro Ile Lys Gly Pro Arg Asp Ile Gln Leu Asp Leu Glu
        385                 390                 395 atg atc act gtc aac act gtc atc aac ttc aga ggc agc tcc gtg atc     1581
Met Ile Thr Val Asn Thr Val Ile Asn Phe Arg Gly Ser Ser Val Ile
    400                 405                 410 cga ctg cgg ata tat gtg tcg cag tat ccg ttc tgagcctctg gctaaggcct   1634
Arg Leu Arg Ile Tyr Val Ser Gln Tyr Pro Phe
415                 420                 425 ctgacactgc ctttcaccag caccgaggga cgggaggaga aaggaaacca gcaagaatga   1694
gagcgagaca gacattgcac ctttcctgct gaatatctcc tgggggcatc agcctagcat   1754
cttgacccat atctgtacta ttgcagatgg tcactctgaa ggacaccctg ccctcagttc   1814
ctatgatgca gttatccaaa agtgttcatc ttagcccctg atatgaggtt gccagtgact   1874
cttcaaagcc ttccatttat ttccatcgtt ttataaaaaa gaaatagat tagatttgct    1934 ggggtatgag tcctcgaagg ttcaaaagac tgagtggctt gctctcacct cttcctctcc   1994
ttcctccatc tcttgctgca ttgctgcttt gcaaaagtcc tcatgggctc gtgggaaatg   2054
ctgggaatag ctagtttgct tcttgcatgt tctgagaagg ctatgggaac acaccacagc   2114
aggatcgaag gttttatag agtctatttt aaaatcacat ctggtatttt cagcataaaa    2174
gaaattttag ttgtctttaa aatttgtatg agtgtttaac cttttcttat tcattttgag   2234
gcttcttaaa gtggtagaat tccttccaaa ggcctcagat acatgttatg ttcagtcttt   2294
ccaacctcat ccttttcctgc atcttagccc agttttacg aagacccctt aatcatgctt    2354
tnttaagagt ttttacccaa ctgcgttgga agacagaggt atccagactg attaaataat   2414
tgaagaaaaa aaaaa                                                    2429
```

<210> SEQ ID NO 8
<211> LENGTH: 461
<212> TYPE: PRT
<213> ORGANISM: Mus musculus
<220> FEATURE:
<221> NAME/KEY: misc_feature
<223> OTHER INFORMATION: Clone mouse A55b derived from Day 13 mouse
      embryonic heart

<400> SEQUENCE: 8

```
Met Gly Pro Arg Ser Phe Glu Pro Met His Ser Gly Leu Cys Arg Gln
    -35                 -30                 -25

Arg Arg Met Ile Leu Thr Val Thr Ile Leu Ala Leu Trp Leu Pro His
-20                 -15                 -10                  -5

Pro Gly Asn Ala Gln Gln Gln Cys Thr Asn Gly Phe Asp Leu Asp Arg
            -1  1                   5                  10

Gln Ser Gly Gln Cys Leu Asp Ile Asp Glu Cys Arg Thr Ile Pro Glu
```

```
                15                  20                  25
Ala Cys Arg Gly Asp Met Met Cys Val Asn Gln Asn Gly Gly Tyr Leu
            30                  35                  40

Cys Ile Pro Arg Thr Asn Pro Val Tyr Arg Gly Pro Tyr Ser Asn Pro
 45                  50                  55                  60

Tyr Ser Thr Ser Tyr Ser Gly Pro Tyr Pro Ala Ala Pro Pro Val
                    65                  70                  75

Pro Ala Ser Asn Tyr Pro Thr Ile Ser Arg Pro Leu Val Cys Arg Phe
                80                  85                  90

Gly Tyr Gln Met Asp Glu Gly Asn Gln Cys Val Asp Val Asp Glu Cys
                95                 100                 105

Ala Thr Asp Ser His Gln Cys Asn Pro Thr Gln Ile Cys Ile Asn Thr
            110                 115                 120

Glu Gly Gly Tyr Thr Cys Ser Cys Thr Asp Gly Tyr Trp Leu Leu Glu
125                 130                 135                 140

Gly Gln Cys Leu Asp Ile Asp Glu Cys Arg Tyr Gly Tyr Cys Gln Gln
                145                 150                 155

Leu Cys Ala Asn Val Pro Gly Ser Tyr Ser Cys Thr Cys Asn Pro Gly
            160                 165                 170

Phe Thr Leu Asn Asp Asp Gly Arg Ser Cys Gln Asp Val Asn Glu Cys
            175                 180                 185

Glu Thr Glu Asn Pro Cys Val Gln Thr Cys Val Asn Thr Tyr Gly Ser
        190                 195                 200

Phe Ile Cys Arg Cys Asp Pro Gly Tyr Glu Leu Glu Glu Asp Gly Ile
205                 210                 215                 220

His Cys Ser Asp Met Asp Glu Cys Ser Phe Ser Glu Phe Leu Cys Gln
                    225                 230                 235

His Glu Cys Val Asn Gln Pro Gly Ser Tyr Phe Cys Ser Cys Pro Pro
                240                 245                 250

Gly Tyr Val Leu Leu Asp Asp Asn Arg Ser Cys Gln Asp Ile Asn Glu
            255                 260                 265

Cys Glu His Arg Asn His Thr Cys Thr Ser Leu Gln Thr Cys Tyr Asn
270                 275                 280

Leu Gln Gly Gly Phe Lys Cys Ile Asp Pro Ile Ser Cys Glu Glu Pro
285                 290                 295                 300

Tyr Leu Leu Ile Gly Glu Asn Arg Cys Met Cys Pro Ala Glu His Thr
                305                 310                 315

Ser Cys Arg Asp Gln Pro Phe Thr Ile Leu Tyr Arg Asp Met Asp Val
            320                 325                 330

Val Ser Gly Arg Ser Val Pro Ala Asp Ile Phe Gln Met Gln Ala Thr
            335                 340                 345

Thr Arg Tyr Pro Gly Ala Tyr Tyr Ile Phe Gln Ile Lys Ser Gly Asn
        350                 355                 360

Glu Gly Arg Glu Phe Tyr Met Arg Gln Thr Gly Pro Ile Ser Ala Thr
365                 370                 375                 380

Leu Val Met Thr Arg Pro Ile Lys Gly Pro Arg Asp Ile Gln Leu Asp
                385                 390                 395

Leu Glu Met Ile Thr Val Asn Thr Val Ile Asn Phe Arg Gly Ser Ser
            400                 405                 410

Val Ile Arg Leu Arg Ile Tyr Val Ser Gln Tyr Pro Phe
            415                 420                 425

<210> SEQ ID NO 9
```

```
<211> LENGTH: 423
<212> TYPE: PRT
<213> ORGANISM: Mus musculus

<400> SEQUENCE: 9

Gln Cys Thr Asn Gly Phe Asp Leu Asp Arg Gln Ser Gly Gln Cys Leu
1               5                   10                  15

Asp Ile Asp Glu Cys Arg Thr Ile Pro Glu Ala Cys Arg Gly Asp Met
            20                  25                  30

Met Cys Val Asn Gln Asn Gly Gly Tyr Leu Cys Ile Pro Arg Thr Asn
        35                  40                  45

Pro Val Tyr Arg Gly Pro Tyr Ser Asn Pro Tyr Ser Thr Ser Tyr Ser
    50                  55                  60

Gly Pro Tyr Pro Ala Ala Ala Pro Pro Val Pro Ala Ser Asn Tyr Pro
65                  70                  75                  80

Thr Ile Ser Arg Pro Leu Val Cys Arg Phe Gly Tyr Gln Met Asp Glu
                85                  90                  95

Gly Asn Gln Cys Val Asp Val Asp Glu Cys Ala Thr Asp Ser His Gln
            100                 105                 110

Cys Asn Pro Thr Gln Ile Cys Ile Asn Thr Glu Gly Gly Tyr Thr Cys
        115                 120                 125

Ser Cys Thr Asp Gly Tyr Trp Leu Leu Glu Gly Gln Cys Leu Asp Ile
    130                 135                 140

Asp Glu Cys Arg Tyr Gly Tyr Cys Gln Gln Leu Cys Ala Asn Val Pro
145                 150                 155                 160

Gly Ser Tyr Ser Cys Thr Cys Asn Pro Gly Phe Thr Leu Asn Asp Asp
                165                 170                 175

Gly Arg Ser Cys Gln Asp Val Asn Glu Cys Glu Thr Glu Asn Pro Cys
            180                 185                 190

Val Gln Thr Cys Val Asn Thr Tyr Gly Ser Phe Ile Cys Arg Cys Asp
        195                 200                 205

Pro Gly Tyr Glu Leu Glu Glu Asp Gly Ile His Cys Ser Asp Met Asp
    210                 215                 220

Glu Cys Ser Phe Ser Glu Phe Leu Cys Gln His Glu Cys Val Asn Gln
225                 230                 235                 240

Pro Gly Ser Tyr Phe Cys Ser Cys Pro Pro Gly Tyr Val Leu Leu Asp
                245                 250                 255

Asp Asn Arg Ser Cys Gln Asp Ile Asn Glu Cys Glu His Arg Asn His
            260                 265                 270

Thr Cys Thr Ser Leu Gln Thr Cys Tyr Asn Leu Gln Gly Gly Phe Lys
        275                 280                 285

Cys Ile Asp Pro Ile Ser Cys Glu Glu Pro Tyr Leu Leu Ile Gly Glu
    290                 295                 300

Asn Arg Cys Met Cys Pro Ala Glu His Thr Ser Cys Arg Asp Gln Pro
305                 310                 315                 320

Phe Thr Ile Leu Tyr Arg Asp Met Asp Val Val Ser Gly Arg Ser Val
                325                 330                 335

Pro Ala Asp Ile Phe Gln Met Gln Ala Thr Thr Arg Tyr Pro Gly Ala
            340                 345                 350

Tyr Tyr Ile Phe Gln Ile Lys Ser Gly Asn Glu Gly Arg Glu Phe Tyr
        355                 360                 365

Met Arg Gln Thr Gly Pro Ile Ser Ala Thr Leu Val Met Thr Arg Pro
    370                 375                 380

Ile Lys Gly Pro Arg Asp Ile Gln Leu Asp Leu Glu Met Ile Thr Val
```

Asn Thr Val Ile Asn Phe Arg Gly Ser Ser Val Ile Arg Leu Arg Ile
385                 390                 395                 400
                405                 410                 415
Tyr Val Ser Gln Tyr Pro Phe
        420

<210> SEQ ID NO 10
<211> LENGTH: 1269
<212> TYPE: DNA
<213> ORGANISM: Mus musculus

<400> SEQUENCE: 10

| | | | | |
|---|---|---|---|---|
| cagtgcacaa | acggctttga | cctggaccgc | cagtcaggac | agtgtctaga tattgatgaa | 60 |
| tgccggacca | tccctgaggc | ttgtcgtggg | gacatgatgt | gtgtcaacca gaatggcggg | 120 |
| tatttgtgca | tccctcgaac | caacccagtg | tatcgagggc | cttactcaaa tccctactct | 180 |
| acatcctact | caggcccata | cccagcagcg | gccccaccag | taccagcttc caactacccc | 240 |
| acgatttcaa | ggcctcttgt | ctgccgcttt | gggtatcaga | tggatgaagg caaccagtgt | 300 |
| gtggatgtgg | acgagtgtgc | aacagactca | caccagtgca | accctaccca gatctgtatc | 360 |
| aacactgaag | gaggttacac | ctgctcctgc | accgatgggt | actggcttct ggaagggcag | 420 |
| tgcctagata | ttgatgaatg | tcgctatggt | tactgccagc | agctctgtgc aaatgttcca | 480 |
| ggatcctatt | cctgtacatg | caaccctggt | ttcaccctca | cgacgatgg aaggtcttgc | 540 |
| caagatgtga | cgagtgcga | aactgagaat | ccctgtgttc | agacctgtgt caacaccctat | 600 |
| ggctcttcta | tctgccgctg | tgacccagga | tatgaacttg | aggaagatgg cattcactgc | 660 |
| agtgatatgg | acgagtgcag | cttctccgag | ttcctctgtc | aacacgagtg tgtgaaccag | 720 |
| ccgggctcat | acttctgctc | gtgccctcca | ggctacgtcc | tgttggatga taaccgaagc | 780 |
| tgccaggata | tcaatgaatg | tgagcaccga | aaccacacgt | gtacctcact gcagacttgc | 840 |
| tacaatctac | aagggggctt | caaatgtatt | gatcccatca | gctgtgagga gccttatctg | 900 |
| ctgattggtg | aaaaccgctg | tatgtgtcct | gctgagcaca | ccagctgcag agaccagcca | 960 |
| ttcaccatcc | tgtatcggga | catggatgtg | gtgtcaggac | gctccgttcc tgctgacatc | 1020 |
| ttccagatgc | aagcaacaac | ccgataccct | ggtgcctatt | acattttcca gatcaaatct | 1080 |
| ggcaacgagg | gtcgagagtt | ctatatgcgg | caaacagggc | ctatcagtgc caccctggtg | 1140 |
| atgacacgcc | ccatcaaagg | gcctcgggac | atccagctgg | acttggagat gatcactgtc | 1200 |
| aacactgtca | tcaacttcag | aggcagctcc | gtgatccgac | tgcggatata tgtgtcgcag | 1260 |
| tatccgttc | | | | | 1269 |

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Primer
<221> NAME/KEY: misc_feature
<223> OTHER INFORMATION: "n" may be a, c, g or t

<400> SEQUENCE: 11
cgattgaatt ctagacctgc ctcgagnnnn nnnnn                                35

<210> SEQ ID NO 12
<211> LENGTH: 27
<212> TYPE: DNA
<213> ORGANISM: Artificial Sequence

```
-continued

<220> FEATURE:
<223> OTHER INFORMATION: Description of Artificial Sequence: A55 R1
      Primer

<400> SEQUENCE: 12
cgtttgtgca ctgctgctgt gcattcc                                              27
```